United States Patent
Weyens et al.

(10) Patent No.: US 10,517,244 B2
(45) Date of Patent: Dec. 31, 2019

(54) METHOD TO DEVELOP HERBICIDE-RESISTANT SUGAR BEET PLANTS

(71) Applicant: SESVanderHave N.V., Tienen (BE)

(72) Inventors: Guy Weyens, Beersel (BE); Marc Lefebvre, Jodoigne Souveraine (BE); Rudiger Hain, Frankfurt (DE); Gerhard Johann, Burscheid (DE)

(73) Assignee: SESVANDERHAVE N.V., Tienen (BE)

( * ) Notice: Subject to any disclaimer, the term of this patent is extended or adjusted under 35 U.S.C. 154(b) by 379 days.

(21) Appl. No.: 14/443,587

(22) PCT Filed: Dec. 13, 2013

(86) PCT No.: PCT/EP2013/076618
§ 371 (c)(1),
(2) Date: May 18, 2015

(87) PCT Pub. No.: WO2014/091021
PCT Pub. Date: Jun. 19, 2014

(65) Prior Publication Data
US 2015/0289464 A1  Oct. 15, 2015

Related U.S. Application Data

(60) Provisional application No. 61/736,817, filed on Dec. 13, 2012.

(30) Foreign Application Priority Data

Dec. 13, 2012 (EP) .................................. 12196858

(51) Int. Cl.
*A01H 4/00* (2006.01)
*C12N 15/82* (2006.01)
*A01H 3/04* (2006.01)

(52) U.S. Cl.
CPC ............. *A01H 4/008* (2013.01); *A01H 3/04* (2013.01); *C12N 15/8274* (2013.01)

(58) Field of Classification Search
CPC . A01H 4/008; A01H 1/06; A01H 3/04; A01H 4/00; A01H 5/00; A01H 1/04; C12N 15/8278; C12N 15/8213; C12N 15/8274; C12N 5/04; C12Y 202/01006
See application file for complete search history.

(56) References Cited

U.S. PATENT DOCUMENTS

| | | | | |
|---|---|---|---|---|
| 5,859,348 A | * | 1/1999 | Penner | A01H 1/04 435/410 |
| 5,969,215 A | * | 10/1999 | Hall | A01H 4/008 800/278 |
| 2007/0074303 A1 | * | 3/2007 | McCutchen | C12N 9/1092 800/278 |
| 2009/0205064 A1 | * | 8/2009 | Schopke | C12N 15/8274 800/260 |

FOREIGN PATENT DOCUMENTS

| | | | |
|---|---|---|---|
| EP | 0257993 A2 | 3/1988 | |
| WO | WO 95/10178 A1 | 4/1995 | |
| WO | WO 2012/049266 A1 | 4/2012 | |
| WO | WO 2012/049268 A1 * | 4/2012 | ............... A01H 5/00 |
| WO | WO-2012049268 A1 * | 4/2012 | ............... A01H 1/04 |
| WO | WO 2012/150335 A1 | 11/2012 | |

OTHER PUBLICATIONS

Hall, Robert D., et al. "Sugar beet guard cell protoplasts demonstrate a remarkable capacity for cell division enabling applications in stomatal physiology and molecular breeding." Journal of experimental botany 48.2 (1997): 255-263.*
Dovzhenko, Alexander, and Hans-Ulrich Koop. "Sugarbeet (*Beta vulgaris* L.): shoot regeneration from callus and callus protoplasts." Planta 217.3 (2003): 374-381. (Year: 2003).*
Hall, Robert D., et al. "Sugar beet guard cell protoplasts demonstrate a remarkable capacity for cell division enabling applications in stomatal physiology and molecular breeding." Journal of experimental botany 48.2 (1997): 255-263. (Year: 1997).*
Duggleby, Ronald G., and Siew Siew Pang. "Acetohydroxyacid synthase." BMB Reports 33.1 (2000): 1-36. (Year: 2000).*
International Preliminary Report on Patentability dated May 26, 2015 for International Patent Application No. PCT/EP2013/076618, filed Dec. 13, 2013.
International Search Report and Written Opinion dated Feb. 28, 2014 for International Patent Application No. PCT/EP2013/076518, filed Dec. 13, 2013.
Written Opinion of the International Preliminary Examining Authority dated Dec. 1, 2014 for International Patent Application No. PCT/EP2013/076518, filed Dec. 13, 2013.
Hall et al.: "Sugar beet Guard Cell Protoplasts Demonstrate a Remarkable Capacity for Cell Division Enabling Application in Stomatal Physiology and Molecular Breeding", Journal of Experimental Botany, vol. 48, No. 307, Feb. 1, 1997 (Feb. 1, 1997), pp. 255-263, XP000893145, ISSN: 0022-0957.
Gurel et al.: "Biotechnology Applications for Sugar Beet", Critical Reviews in Plant Sciences, vol. 27, No. 2, 2008, pp. 108-140, XP009167608.
Dyer et al.: "Potential Benefits and Risks of Herbicide-Resistant Crops Produced by Biotechnology", in: "Horticultural Reviews", 1993, John Wiley & Sons, XP002693215.

(Continued)

*Primary Examiner* — Weihua Fan
(74) *Attorney, Agent, or Firm* — Merchant & Gould P.C.

(57) ABSTRACT

A method for producing herbicide-resistant sugar beet plant includes obtaining protoplasts from stomatal guard cells isolated from a sugar beet plant. A composition having an ALS herbicide is applied to the cells at a concentration which is lethal to the cells. Sugar beet plants are regenerated from the surviving cells.

21 Claims, 1 Drawing Sheet
Specification includes a Sequence Listing.

(56) References Cited

OTHER PUBLICATIONS

Rey et al.: "Atrazine and Diuron Resistant Plants from Photoautotrophic Protoplast-Derived Cultures of *Nicotiana plumbaginfolia*", Plant Cell Reports, vol. 9, No. 5, 1990, pp. 241-244, XP009167607.
Horikoshi et al.: "Selection of Tobacco Cell Lines Resistant to Photobleaching Herbicides", Journal of Pesticide Science, vol. 24, No. 1, 1999, pp. 13-16, XP009167605, ISSN: 0385-1559.
Tan et al.: "Imidazolinone-Tolerant Crops: History, Current Status and Future", Pest Management Science, vol. 61, No. 3, Jan. 1, 2005 (Jan. 1, 2005), pp. 246-257, XP009058795, ISSN: 1526-498X.
Duggleby et al.: "Structure and mechanism of inhibition of plant acetohydroxyacid synthase", Plant Physiology and Biochemistry, Gauthier-Villars, Paris, FR, vol. 46, No. 3, Jan. 14, 2008 (Jan. 14, 2008), pp. 309-324, XP022550175, ISSN: 0981-9428.
Duggleby et al.: "Acetohydroxyacid Synthase", Journal of Biochemistry and Molecular Biology, vol. 33, No. 1, Jan. 1, 2000 (Jan. 1, 2000), pp. 1-36, XP001119823, ISSN: 1225-8687.
Alexander Dovzhenko, "Towards plastid transformation in rapeseed (*Brassica napus* L.) and sugarbeet (*Beta vulgaris* L.)", Dissertation, Ludwig-Maximilians-University of Munich: Faculty of Biology, 2001, 142 pages.

\* cited by examiner

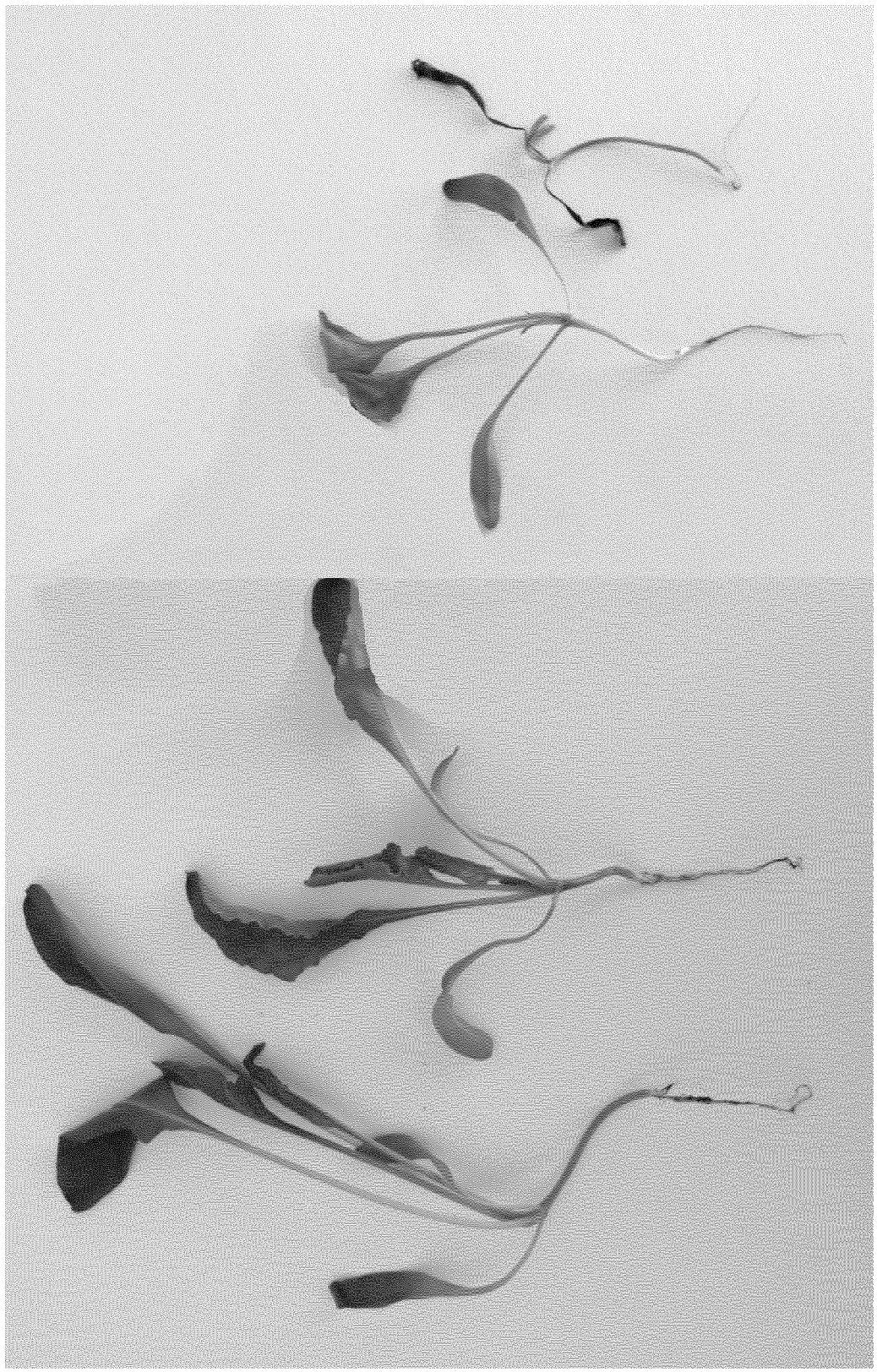

METHOD TO DEVELOP HERBICIDE-RESISTANT SUGAR BEET PLANTS

This application is a National Stage Application of PCT/EP2013/076618, filed Dec. 13, 2013, which claims benefit of Ser. No. 12/196,858.0, filed Dec. 13, 2012 in Europe, and also claims the benefit of Ser. No. 61/736,817, filed Dec. 13, 2012 in the United States, and which applications are incorporated herein by reference. To the extent appropriate, a claim of priority is made to each of the above disclosed applications.

FIELD OF THE INVENTION

The present invention relates to a method to generate sugar beet plants resistant to herbicides, for instance inhibitor(s) of the acetohydroxyacid synthase enzyme (ALS).

The present invention further relates to the plants that are obtained by this method.

Sugar beet is an important agricultural crop in temperate and subtropical regions.

In modern agriculture, herbicides are widely used to manage weeds proliferation.

The development of sugar beet plants resistant towards herbicide(s) such as ALS inhibitors can be undertaken by using transgenic approaches.

Indeed, the introduction of foreign DNA carrying a gene conferring resistance towards an herbicide has been successfully performed in a variety of field crops, including in sugar beet.

WO 95/10178 discloses a transgenic-induced resistance to the herbicide Bialaphos. The gene encoding the resistance is introduced in protoplasts of guard cells from sugar beet, then these protoplasts are regenerated into sugar beet plants. Those plants are further resistant to the chemical phosphinothricin and its derivative glufosinate.
Non transformed plants did not acquire resistance to Bialaphos.

At best, 28 transformed calli were regenerated from 83000 protoplasts; at worst, 1 callus was regenerated from 190 000 protoplasts. Subsequently, some of these calli can show somatic embryogenesis and can regenerate sugar beet plantlets, with an efficiency of 1% and, a characteristic found very advantageous, up to 30%.

This approach, is nevertheless not commonly used in the art, which widely relies on the more direct transformation of calli from explants obtained from sugar beet organs such as embryos and/or from leaf discs.

There still exists an important need to develop herbicide-resistant plants such as in the sugar beet crop and that without relying on DNA vectors and/or on the insertion of foreign genes.

On the other hand, the development of a sugar beet resistant plant towards herbicide(s), such as ALS inhibitors can theoretically be undertaken via classical breeding with a sugar beet plant which would contain a naturally-occurring resistance gene. However, such approach is time consuming and, to the applicants' best knowledge, did not result into success, despite the fact that naturally-occurring ALS inhibitor-resistant plants were documented, at least for species other than sugar beet including a variety of weed species. Especially a double mutant (i.e a plant having two mutations in the same ALS gene) is very unlikely to occur in nature.

The patent application WO 98/02527 discloses a method for the manufacture of sugar beet plant resistant to some ALS inhibitors, such as sulfonylurea herbicides, which comprises the steps of exposing to sulfonylurea calli obtained from explants of *B. vulgaris*, and regenerating plants from the few spontaneous mutants that can grow in the presence of this herbicide.

This method yielded a plant having a mutation in the ALS gene, where the proline at position 188 of the encoded ALS enzyme (corresponding to the 197 position of the *Arabidopsis thaliana* ALS enzyme) is substituted by a serine. However, this mutant is not commercially used because treatments with the preferred modern sulfonylureas ALS herbicides (e.g. foramsulfuron) exhibit some phytotoxicity in field trials at the necessary dose rate.

The patent application WO 2012/049268 relies on the same method, except that calli obtained from explants of *B. vulgaris* are exposed to foramsulfuron, and thus resulted into sugar beet plant resistant to several ALS inhibitors, including to foramsulfuron.

This method yielded a plant having a mutation in the ALS gene, where the tryptophan at position 569 of the encoded ALS enzyme (corresponding to the 574 position of the *Arabidopsis thaliana* ALS enzyme) is substituted by a leucine.

Field trials of this homozygote 569/569 mutant showed good resistance to foramsulfuron, to iodosulfuron (another ALS inhibitor), as well as to mixtures of different ALS inhibitors.

Both these published methods take benefit from the well-established steps of isolation of calli from individual explants such as embryos. However, this is a time-consuming approach involving (i) isolation of large number of fresh embryos, (ii) their repeated culture on agar-solidified culture medium, and (iii) the selection of the regenerable calli using morphological selection approaches.

Other strategies to transfer genetic traits to sugar beet have been developed and rely on mesophyll protoplasts (which are different of stomatal guard cell protoplasts) as starting material (Krens et al., 1990, Theor. appl. Genet., vol 79, pages 390-396). Gurel et al. 2008, Critical reviews in Plant Science, 27, 108-140, discloses biotechnology applications for sugar beet. Seven different in vitro culture techniques are disclosed. Among them is the culture of protoplasts either from stomatal guard cells for transformation purposes, or from friable callus from etiolated hypocotyl explants, the latter being much more efficient. This approach using protoplasts is however associated to major difficulties.
Hall et al. 1997, J. Exp. Botany, 48, 255-263 have used a culture of 500000 stomatal guard cell protoplasts for carrying a transformation experiment with foreign DNA. The transformation efficiency was higher than 2%. On the other hand, in vitro culture of plants is reported to be associated to stomatal failure, pointing to problems in the corresponding cells and thus to the production of very high amount of stomatal guard cell protoplasts, such as amounts needed for carrying a method involving a mutational event.

SUMMARY OF THE INVENTION

In a broad aspect, the present invention discloses a method for producing a mutant sugar beet plant being resistant to an herbicide comprising the steps of:
obtaining protoplasts from stomatal guard cells isolated from a sugar beet plant;
applying to an in vitro culture of these protoplasts a composition comprising this herbicide at a concentration that is lethal to more than 99% of the in vitro cultured cells; and regenerating sugar beet plants from the surviving cells of these in vitro cultured cells, possibly selecting regenerated sugar beet plants having a mutation in the gene encoding the peptide(s) targeted by this herbicide, wherein these stomatal guard cells protoplasts are pre selected for their capacity to regenerate into a sugar beet plant, and wherein this herbicide is applied to more than 20 000 000 of these protoplasts.

The herbicide used in the present method can be an herbicide not targeting ALS gene.

The preferred herbicides (not targeting ALS) are selected from the group consisting of:

4-HPPD inhibitors (such as mesotrione, isoxaflutole, pyrasulfotole, benzobicyclon, benzofenap, pyrazolynate, pyrazoxyfen, tembotrione, topramezone, sulcotrione and sulcotrion), inhibitors of the carotenoid biosynthesis (such as flurtamone, fluridone, flurochloridone, beflubutamid, norflurazon, picolinafen and diflufenican);

inhibitors of EPSP synthase (such as glyphosate or glyphosate-trimesium);

inhibitors of phosphosystem II (such as Phenyl-carbamates (for instance phenmedipham or desmedipham), Pyridazinones (for instance chloridazon=pyrazon), Triazines (for instance cyanazine, remtal, eglinazine-ethyl, proglinazine-ethyl, ametryn, atrazine, desmetryn, dimethametryn, prometon, prometryn, propazine, simazine, simetryn, terbumeton, terbuthylazine, terbutryn, methoprotyn), Triazinones (for instance metamitron, metribuzin, hexazinone, metribuzin), Uracils (bromacil, lenacil, terbacil), Ureas (dimefuron, isoproturon, linuron, monolinuron, ethidimuron, methabenzthiazuron, tebuthiuron, diuron, fenuron, neburon, siduron, isouron, chlorobromuron, chlorotoluron, chloroxuron, fluometuron, metobromuron metoxuron, thiazafluron, monuron, cycluron, monolinuron), or amicarbazone, solan, propanil, bentazon, bromoxynil, ioxynil, bromofenoxim, pyridate, pyridafol;

inhibitors of phosphosystem I (such as diquat or paraqua);

inhibitors of cell division (such as carbetamide, chlorpropham, propham, naproanilide, diphenamid, napropamide, butenachlor, metazachlor, diethatyl-ethyl, acetochlor, alachlor, butachlor, propachlor Monsanto, propisochlor, dimethachlor, dimethenamid, metolachlor, pretilachlor, S-metolachlor, pethoxamid, thenylchlor, anilofos, cafenstrole, indanofan, bromobutide, piperophos, flufenacet, mefenacet, fentrazamide);

inhibitors of microtubule assembly (such as propyzamide=pronamide, tebutam, chlorthal-dimethyl=DCPA, fluchloralin, pendimethalin, butralin, benefin=benfluralin, ethalfluralin, oryzalin, trifluralin, prodiamine, dinitramine, butamifos, dithiopyr, thiazopyr);

inhibitors of protoporphyrinogen oxidase (such as Diphenylethers (acifluorfen-sodium, bifenox, ethoxyfen-ethyl, chlornitrofen, fluoroglycofen-ethyl, oxyfluorfen, chlomethoxyfen, fluordifen, fomesafen, lactofen, nitrofen, aclonifen), N-phenylphthalimides (cinidon-ethyl, flumiclorac-pentyl, flumioxazin, flumiclorac-pentyl), Oxadiazoles (oxadiargyl, oxadiazon) Oxazolidinediones, (pentoxazone), Phenylpyrazoles (fluazolate, fluazolate, pyraflufen-ethyl), Pyrimidindiones (saflufenacil, benzfendizone, butafenacil), Thiadiazoles (thidiazimin, fluthiacet-methyl), Triazolinones (azafenidin, carfentrazone-ethyl sulfentrazone), pyraclonil, profluazol, flufenpyr-ethyl);

inhibitors of Acetyl CoA carboxylase (such as Aryloxyphenoxypropionates (such as clodinafop-propargyl, cyhalofop-butyl, diclofop-methyl, fenoxaprop-P-ethyl, fluazifop-P-butyl, haloxyfop-etotyl, haloxyfop-methyl, haloxyfop-P-methyl, propaquizafop, quizalofop-P-ethyl or quizalofop-P-tefuryl), Cyclohexanediones (such as alloxydim, butroxydim, clethodim, cycloxydim, profoxydim, sethoxydim, tepraloxydim or tralkoxydim) or Phenylpyrazoline (pinoxaden));

cell wall synthesis inhibitors (such as indaziflam, isoxaben, chlorthiamid, dichlobenil, quinclorac or flupoxam);

inhibitor of glutamine synth(et)ase (glufosinate-ammonium or bialaphos=bilanaphos) and synthetic auxin (such as TBA, dicamba, chloramben, benazolin-ethyl 4, dichlorprop-P, mecoprop-P, 2,4,5-T (Weedar) 2,4-D (Weedar), 2,4-DB (Butyrol), dichlorprop, MCPB, mecoprop, MCPA-thioethyl, clomeprop, Agroxone 4, aminopyralid, clopyralid, fluroxypyr, halauxifen-methyl, picloram, triclopyr, quinclorac or quinmerac), more preferably from the group consisting of 4-HPPD inhibitors, inhibitors of the carotenoid biosynthesis, inhibitors of EPSP synthase, inhibitors of phosphosystem II, inhibitors of phosphosystem I, inhibitors of microtubule assembly, inhibitors of protoporphyrinogen oxidase and synthetic auxin.

Another highly preferred herbicide is an ALS inhibitor.

Therefore, the present invention relates to a method for producing a mutant sugar beet plant being resistant to one or more inhibitor(s) of the acetohydroxyacid synthase enzyme (ALS) comprising the steps of:

obtaining protoplasts from stomatal guard cells isolated from a sugar beet plant;

applying to an in vitro culture of the said protoplasts a composition comprising one or more ALS inhibitor(s) at a concentration that is lethal to (more than 99% (preferably more than 99.9% or even more than 99.99%) of) the in vitro cultured cells (yet allowing some mutants to escape); and regenerating sugar beet plants from the surviving cells of the said in vitro cultured cells, wherein the said stomatal guard cells protoplasts are pre selected for their capacity to regenerate into a sugar beet plant and/or wherein the said ALS inhibitor(s) is/are applied to more than 2 000 000 (preferably more than 10 000 000, more preferably to more than 20 000 000 or even more than 50 000 000) of the said protoplasts.

Preferably this method comprises the sub-steps of isolating stomatal guard cells protoplasts from sugar beet plants of different genotypes and measuring for each genotype the proportion of the said protoplasts that is growing when the said protoplasts are put in culture.

Preferably this method further comprises the step of sequencing the genome of the regenerated plants from the surviving in vitro cultured cells, advantageously for identifying a mutation in the ALS gene and/or for selecting regenerated sugar beet plants having one or more, preferably one, two, or more mutations in the ALS gene.

Advantageously, sugar beet having one or several mutation(s) in the ALS gene at positions encoding the amino acids selected from the group consisting of Glycine 112, Alanine 113, Methionine 115, Arginine 133, Valine 187, Arginine 190, Alanine 196, Phenylalanine 197, Lysine 247, Methionine 346, Histidine 347, Arginine 368, Aspartate 370, Aspartate 371, Arginine 372, Methionine 565, Valine 566, Phenylalanine 573, Serine 648 and Glycine 649, preferably selected from the group consisting of Alanine 196, Aspartate 371, Arginine 372, Serine 648 and Glycine 649, are obtained and/or selected by the method of the present invention. Another preferred sugar beet plant having a mutation of the Proline at position 188 and of the Tryptophan at position 569 is obtained and/or selected by the method of the present invention.

Preferably, sugar beet having two or more mutations has two mutations in one allele, meaning that the encoded peptide harbours two mutations synergizing the resistance towards ALS inhibitors (especially towards compositions comprising several ALS inhibitors). An examples of most preferred sugar beet is a sugar beet having a mutation of the Proline at position 188 and of the Tryptophan at position 569 in one allele (and possibly the same mutations in the second allele; alternatively, the second allele harbours different mutations).

Alternatively, sugar beet having two mutations has one mutations on each allele.

The method of the present invention allows to regenerate a sugar beet plant having one mutation in the ALS gene at positions encoding Proline 188 and one or more mutation(s) in the ALS gene at positions encoding Glycine 112, Alanine 113, Methionine 115, Arginine 133, Valine 187, Arginine 190, Alanine 196, Phenylalanine 197, Lysine 247, Methionine 346, Histidine 347, Arginine 368, Aspartate 370, Aspartate 371, Arginine 372, Methionine 565, Valine 566, Tryptophan 569 (preferably mutated into Glycine), Phenylalanine 573, Serine 648 and Glycine 649. An examples of preferred sugar beet is a sugar beet having a mutation of the Proline at position 188 and of another mutation (possibly not the tryptophan 569 or the Trp569Gly) in the same allele.

The method of the present invention allows to regenerate a sugar beet plant having one mutation in the ALS gene at position encoding Tryptophan 569 (preferably mutated into Leucine) and one or more mutation(s) in the ALS gene at positions encoding Glycine 112, Alanine 113, Methionine 115, Arginine 133, Valine 187, Proline 188 (preferably mutated into Threonine, Arginine, Leucine, Glutamine or Alanine), Arginine 190, Alanine 196, Phenylalanine 197, Lysine 247, Methionine 346, Histidine 347, Arginine 368, Aspartate 370, Aspartate 371, Arginine 372, Methionine 565, Valine 566, Phenylalanine 573, Serine 648 and Glycine 649.

An examples of preferred sugar beet is a sugar beet having a mutation of the tryptophan at position 569 and of another mutation (possibly not the Proline 188 or the Pro188Ser) in the same allele.

The method of the present invention allows to regenerate a sugar beet plant having one or more mutation(s) in the ALS gene, wherein the said one or more mutation is selected from the group consisting of Alanine 113 Proline 188, Alanine 196, Aspartate 371, Arginine 372, Tryptophan 569, Serine 648 and Glycine 649, wherein the said Alanine 113 is mutated into Valine or Threonine, wherein the said Proline 188 is mutated into Threonine, Arginine, Leucine, Glutamine or Alanine, wherein the said Alanine 196 is mutated into Valine, wherein the said Aspartate 371 is mutated into Glutamate, wherein the said Arginine 372 is mutated into Histidine, wherein the said Tryptophan 569 is mutated into Glycine, wherein the said Serine 648 is mutated into Threonine and wherein the said and Glycine 649 is mutated into Aspartate.

Preferably, sugar beet having two or more of these specific mutations has two mutations in one allele, meaning that the encoded peptide harbours two mutations synergizing the resistance towards ALS inhibitors (especially towards compositions comprising several ALS inhibitors).

The method of the present invention allows to regenerate a sugar beet plant having one mutation in the ALS gene at position encoding Proline 188 and one mutation in the ALS gene at position encoding Tryptophan 569.

Advantageously, this method comprises a preliminary step of deducing the concentration of the one or more ALS inhibitor(s) at which the composition (comprising the one or more ALS inhibitor(s)) is lethal for at least 99% (preferably at least 99.9% or even 99.99%) of the in vitro cultured cells (yet allowing some mutants to escape).

The preferred ALS inhibitor present in the composition (the said composition comprising in addition another ALS inhibitor, being preferably from another class than sulfonylurea ALS inhibitor, such as thiencarbazone-methyl) to be added to the in vitro cultured stomatal guard cell protoplasts is foramsulfuron, preferably at a concentration of $10^{-9}$ mol/l to (more preferably) $10^{-6}$ mol/l.

Another suitable ALS inhibitor present in the composition to be added to the in vitro cultured stomatal guard cell protoplasts is ethoxysulfuron (possibly this composition further comprises other ALS inhibitors).

A related aspect of the present invention is a mutated sugar beet plant obtainable by the method of the present invention, such as a sugar beet having a mutation at tryptophan 569 and/or at proline 188.

Another related aspect of the present invention is a mutated sugar beet plant comprising SEQ.ID.NO:3 (or SEQ.ID.NO:4) and/or SEQ.ID.NO:5 (or SEQ.ID.NO:6).

A preferred sugar beet plant according to the present invention correspond to the deposit under NCIMB 42050 or NCIMB 42051.

The present invention is also related to tissue or plant part (for instance stomatal guard cells or leaf strips) or seeds derived from the mutated plant of the invention, as well as to their use for the introduction of another genetic trait.

The present invention is also related to the use of the (well regenerating) stomatal guard cell protoplasts developed in the present invention for the introduction of another genetic trait than resistance to ALS inhibitors.

DETAILED DESCRIPTION OF THE INVENTION

The inventors have discovered that protoplasts from stomatal guard cell of sugar beet represent a good starting material for inducing resistance towards herbicides such as ALS inhibitors, despite the fact that regeneration of a sugar beet plant from a stomatal guard cell protoplast is very difficult, of low occurrence, and requires longer and more complex procedures than the direct regeneration from calli obtained from explants, as usually used in the art.

Indeed, callus (calli) from explants is (are) a mass of non-differentiated (or dedifferentiated) cells, which, under appropriate culture conditions, will differentiate (or re-differentiate) and regenerate a wholly functional sugar beet plant. In such method, seeds are collected in large amounts, then easily sterilized and explants are thus obtained in large amounts. Such method is convenient as allowing to perform a large part of the work without the difficulties of a sterile environment.

On the other hand, the stomatal guard cells have a well-defined organization in the plant, and their isolation from the plant tissue results into individual cell(s), then after a treatment into individual protoplasts.

In the method of the present invention, plantlets must be grown in vitro and maintained under sterile conditions, then stomatal guard cells are isolated from these small plantlets and protoplasts are obtained while maintaining sterile conditions, then these individual protoplasts are induced to produce again their cell wall, to grow firstly into micro-calli, then into a sugar beet plant.

Stomatal guard cells protoplasts of sugar beet were found to be very vulnerable, reducing the scope of their application: for instance addition of a mutagen, instead of favouring the appearance of a desired genetic trait, was found to be lethal to the protoplasts in many cases.

In other words, it was completely unexpected to succeed in using stomatal guard cell protoplasts as a starting material for developing a sugar beet plant having acquired a desired genetic trait through mutation.

Furthermore, the inventors have found that the capacity of stomatal guard cell protoplasts to divide is very dependent on sugar beet genotypes: the stomatal guard cell protoplasts from the majority of the genotypes exhibit a very low (almost zero) capacity to divide (grow), while the protoplasts from some specific genotypes have a sizable capacity to grow in vitro.

The inventors have identified that the culture on solid medium (polymer-containing medium, such as alginate or agarose-like containing medium) of very large amounts of these stomatal guard cell protoplasts, then the exposure of the cultured material (normally in the form of regenerated calli) to herbicides such as ALS inhibitor(s) resulted into the selection of some mutated cells being resistant to this herbicide molecule, despite the fact that, in absence of added mutagens, spontaneous mutations are known to be very rare, and that the method cannot take benefit of the genetic diversity within a population, in selecting an already existing mutant plant exhibiting the desired resistance towards one or more ALS inhibitors.

Some of these mutated cells having acquired resistance towards herbicides such as ALS inhibition were further able to regenerate into viable sugar beet plant(s). Although protoplasts are very difficult to use in practice, the present method nevertheless yielded very rapidly stable mutants having acquired resistance towards the herbicide.

The method of the present invention allows the production of herbicide-resistant (ALS inhibitor-resistant) sugar beet plants having one or several mutations, including one or several mutations in the enzyme being the target of the herbicide, for instance an ALS inhibitor (such as a mutation of the ALS gene, wherein the ALS gene encodes an ALS protein containing an amino acid different from tryptophan at position 569 of the ALS protein; corresponding to position 574 of the *Arabidopsis thaliana* ALS), possibly in addition to at least another mutation in this gene and/or to other mutations in other genes.

An aspect of the present invention is therefore a method for producing sugar beet plant (*Beta vulgaris*; thus also *Beta vulgaris maritima* ssp) resistant to one or more ALS inhibitor(s) comprising the steps of:
  obtaining (protoplasts from) stomatal guard cells isolated from a sugar beet plant (sensitive to ALS inhibitors);
  applying to these in vitro cultured cells a composition comprising one or more ALS inhibitors at a concentration that is lethal to these in vitro cultured cells (at least 99% of the (wild-type) cells are killed by the ALS inhibitor, but some mutants can escape the treatment); and
regenerating sugar beet plants from the surviving cells.

This method can be seen as an alternative to the introduction of a transgene (for instance disclosed in WO 95/10178). However, a method based on mutation of endogenous gene(s) is more laborious by comparison to a transgenic approach. Indeed, the introduction of a transgenic (mutated) gene is much more rapid, flexible and predictable.

The absence of transgene-induced resistance refers to the fact that the acquired resistance to the ALS inhibitor(s) is not directly caused by the in vitro insertion of a (foreign) DNA into the stomatal guard cells protoplasts (or into the cells obtained thereof), such as a (foreign) DNA encoding a protein directly providing resistance to the ALS inhibitor(s), such as a protein locally reducing the toxicity of the ALS inhibitor(s) (e.g. an enzyme degrading the ALS inhibitor(s) or reducing its intracellular concentration), or an ALS protein being resistant to ALS inhibitor(s), such as an ALS mutant enzyme that retains significant activity and functionality even in the presence of the inhibitor(s).

However, the plant obtained by the method of the invention can further be crossed with a transgenic plant in order to stack another genetic trait in the progeny. The plant (or a part thereof) obtained by the present invention can further be used in a subsequent transgenic method to introduce another genetic trait (different from the genetic trait obtained in the method of the present invention).

Possibly, this method further comprises the step of adding a mutagen agent to the culture of the isolated stomatal guard cell protoplasts.

Suitable mutagen agents are physical (such as UV or X-ray) exposure or exposure to chemical agents (such as Ethyl Methane Sulfonate (EMS), for instance at 0.05%, 0.1%, 0.15%, 0.2% or even at 2.5%). However, protoplasts viability was shown to be detrimentally affected by some mutagenesis treatments usually performed, such as treatment of more than 0.2% EMS.

Alternatively, this method thus does not comprises the step of adding a mutagen agent.

In the context of the present invention, an herbicide preferably refers to any molecule, which, when applied at a given dose, is used for weed control.

Preferred herbicides used in the present method (for developing sugar beet plants resistant to this herbicide) have a specific known activity on one peptide (so that a single mutation in the corresponding gene can confer resistance towards this herbicide). In other words, the preferred herbicides are specific for one peptide target (usually inhibiting specifically the activity of one plant enzyme) and/or their target peptide is known (so as to be in a position to screen the resistant sugar beet for a mutation in the target gene)

In the context of the present invention, an ALS inhibitor refers to any molecule inhibiting the function of the ALS gene.

Preferably, the ALS inhibitor(s) used in the present invention (substantially) do not inhibit other (sugar beet) enzymes than ALS.

Advantageously, the ALS inhibitor(s) are selected and used in the present invention at a concentration where more than 90% (more than 95%, more than 99%, more than 99.9%) of the function of the wild-type ALS enzyme is inhibited, but substantially not affecting the function of non-related enzymes.

Suitable ALS inhibitors (for carrying the method) are selected from the group consisting of sulfonylurea herbicides, sulfonylaminocarbonyltriazolinone herbicides, imidazolinone herbicides, triazolopyrimidine herbicides and pyrimidinyl(thio)benzoate herbicides. Advantageously, the herbicide composition comprises at least one sulfonylurea herbicides and at least one triazolopyrimidine.

The preferred ALS inhibitors (for carrying the method) are foramsulfuron, amidosulfuron, thiencarbazone-methyl, ethoxysulfuron and mixture thereof (especially a composition comprising thiencarbazone-methyl and either foramsulfuron or amidosulfuron); however, the regenerated sugar beet mutant is advantageously resistant towards several ALS inhibitors.

Other ALS inhibitors (including mixtures of ALS inhibitors) can be used, and the skilled person knows which mutation provides strong resistance to a given ALS inhibitor (e.g. the mutation of the tryptophan at position 569 is known to be associated to foramsulfuron resistance); hence, given the flexibility and the efficacy of the present method, the skilled person can design sugar beet plants having acquired several mutations and thus broader resistance towards herbicides such as ALS inhibitors (e.g. mixtures of ALS inhibitors).

More preferably, this method comprises a preliminary step of selecting a sugar beet plant genotype (line) for its capacity of the stomatal guard cells protoplasts to regenerate into a fully functional sugar beet plant, and/or the method of the present invention is carried on stomatal guard cells protoplasts isolated from well-regenerating sugar beet genotypes (lines).

A suitable preliminary step (of selecting sugar beet plant genotypes for the ability of their stomatal guard cells protoplasts cells to regenerate into a sugar beet plant) involves the comparison (independently of their possible advantageous features such as yield or resistance towards parasitic infections) of at least 10 different sugar beet plant genotypes (from different genotype backgrounds), preferably at least 15 different genotypes, or even at least 30 different genotypes, for the capacity of their stomatal guard cells protoplasts to regenerate into a sugar beet plant (much more preferably their capacity to grow in vitro and/or to form calli), and the selection of a well-regenerating genotype (line) for carrying the method of the present invention.

In the context of the present invention, well-regenerating stomatal guard cells protoplasts refer to protoplasts having a probability of more than 0.25% (number of growing protoplasts:total protoplast number put into culture; growing: total), preferably more than 1% (growing:total), more preferably more than 5% (growing:total), still more preferably more than 10% (growing:total) or even more than 20% (growing:total) or 50% (growing:total) to divide and/or to grow and/or regenerate into viable sugar beet callus (when grown in the suitable culture media and without exogenous selection pressure such as the toxic molecule/herbicide to be applied in the method of the present invention).

Callus (calli) refers to a mass of undifferentiated cells. In the art, calli can be obtained from explants such as embryos, or parenchyme-derived explants from leaves or cotyledon. However, in the context of the present invention, calli are the result of the growth of (well-regenerating) stomatal guard cells protoplasts.

Advantageously, the calli obtained by these well-regenerating protoplasts have more than 10% (number of calli producing shoots:total calli number; shoots:total), preferably more than 20% (shoots:total) or even more than 30% (shoots:total) of capacity to develop shoots.

Preferably, well-regenerating sugar beet stomatal guard cells protoplasts refer to protoplasts having more than 0.1% (sugar beet plant:total protoplast number) (more preferably more than 1%) of capacity to regenerate into a viable sugar beet plant.

Also preferably, in this method, the composition comprising the herbicide (e.g. one or more ALS inhibitor(s)) is applied to an in vitro culture of more than 2 000 000 of these (well-regenerating) sugar beet stomatal guard cells protoplasts.

Alternatively, or more preferably in addition to the pre-selection step, the composition comprising the herbicide (e.g. one or more ALS inhibitor(s)) is applied to an in vitro culture of more than 5 000 000, or even more than 10 000 000, 20 000 000, or 50 000 000, of these (well-regenerating) sugar beet stomatal guard cells protoplasts.

Preferably, at least 50 000, such as about 100 000, (well-regenerating) stomatal guard cells protoplasts per millilitre were grown onto polymer-containing medium (such as alginate- or agarose-containing medium).

Possibly, these, (well-regenerating) sugar beet stomatal guard cells protoplasts are grown for at least about one week (preferably about 3 weeks and/or of less than 4 weeks) on polymer (alginate)-containing medium, before the application of the composition comprising the herbicide (e.g. one or more) ALS inhibitor(s) such as foramsulfuron and possibly thiencarbazone-methyl).

Preferably, this method further comprises the step of comparing the growth of mutated stomatal guard cell and the growth of wild-type stomatal guard cell (and/or naive and/or not yet herbicide-treated) on a medium that does not comprise ALS inhibitor, and possibly of selecting mutant(s) keeping at least 75% of the growth, preferably at least 90% of the growth of the corresponding wild-type cell.

Preferably, or in addition this method further comprises the step of comparing the growth and/or the yield of the regenerated sugar beet from the mutated cell and the growth and/or the yield of the wild-type (and/or naive and/or not yet treated by the ALS inhibitor) sugar beet in greenhouse assays and in agronomic conditions without any ALS inhibitor, and possibly of selecting ALS inhibitor-resistant mutant(s) sugar beet plants keeping at least 75% of the growth and/or of the yield, preferably at least 90% of the growth and/or of the yield of the wild-type sugar beet.

Preferably, this method further comprises the step of sequencing the regenerated plants from the surviving protoplasts and/or of identifying one or several mutation(s) that are (can be) associated to the resistance to the herbicide (e.g. one or more ALS inhibitor(s)).

In the context of the present invention, the term 'mutation' preferably refers to one (one single) change in the nucleotide sequence encoding the peptide targeted by the herbicide (e.g. the ALS protein) that causes one change in the corresponding amino acid, such that the resulting plant has acquired some resistance towards the herbicide such as ALS inhibitors. In other words, in the context of the present invention, 'mutation' is preferably understood as equivalent to a 'point mutation' that allows some resistance to the herbicide (the ALS inhibitor). Accordingly, "several mutations" preferably refers, in the present invention, to (a stack of) multiple point mutations, each point mutation causing a change of the encoded amino acid so as to provide some resistance to an herbicide (e.g. an ALS inhibitor and/or an herbicide not an ALS inhibitor). Therefore, preferably, in the context of the present invention 'mutation' does not comprise change in the nucleotide sequence that do not modify the encoded protein (such as a change in the third amino acid of a coding triplet), change in amino acids that are not associated to herbicide (such as ALS inhibitor) resistance, nor multiple simultaneous changes in the nucleotide sequence.

Advantageously, this identification step of the mutation(s) associated to the resistance towards the (one or more) ALS inhibitor(s) (preferably one or two mutation(s) in the ALS gene) is coupled to the development of oligonucleotide primers spanning over this mutation.

Advantageously, this identification step of the mutation(s) in the ALS gene is followed by (in vitro) enzymatic activity measurements of the protein encoded by the wild-type and by the mutated ALS genes.

Preferably, these enzymatic measurements of the wild-type ALS enzyme and of the mutated ALS enzyme are performed in the presence of one or more ALS inhibitors (at one or at several concentrations in order to derive an inhibition curve).

Possibly, these enzymatic measurement of the wild-type enzyme and of the mutated enzyme are (further) performed in absence of ALS inhibitors (to compare the enzymatic activity of the mutated enzyme; preferably, in absence of the ALS inhibitor, the mutated enzyme keeps at least 50% of the activity of the wild-type enzyme, more preferably at least 75%, still more preferably at least 90%, at least 95% or even at least 99%).

Preferably, the method of the present invention comprises a step of comparing compositions comprising one or more ALS inhibitors at different concentrations, and deducing the concentration at which the ALS inhibitor, and/or ALS inhibitor in a special formulation within this composition, is/are lethal for an in vitro culture of the stomatal guard cell protoplast isolated from the sugar beet plant (such as stomatal guard cell protoplasts grown on alginate for at least one week).

For instance, this step of deducing the concentration at which the (one or more) ALS inhibitor(s) is/are lethal for stomatal guard cell protoplast isolated from the sugar beet plant is performed on an in vitro culture of the stomatal guard cell protoplasts isolated from the wild-type sugar beet plant (and/or naive and/or not yet treated by the ALS inhibitor).

In the context of the present invention, the lethal concentration of the composition comprising (one or more) ALS inhibitor(s) refers to a concentration sufficient to kill at least 99%, preferably at least 99.9%, more preferably at least 99.99% of the cultured cells (yet allowing some mutants to escape this treatment).

Alternatively, or in addition, this step of deducing the concentration at which the (one or more) ALS inhibitor(s) is lethal for an in vitro culture of the stomatal guard cell protoplasts isolated from the sugar beet plant is (further) performed on an in vitro culture of mutated stomatal guard cells (on cells having acquired a mutation in the ALS gene and being resistant to ALS inhibitor(s)).

The comparison of the lethal concentration of the ALS inhibitor (in a composition comprising this ALS inhibitor) on the naive and on the mutated cells is advantageously expressed as a ratio (or as several ratios, one ratio per ALS inhibitor tested).

Preferably, for one ALS inhibitor, the lethal concentration on naive cell(s) is 50-fold lower than the lethal concentration on mutated cell(s), more preferably, the lethal concentration on naive cell(s) is 200-fold lower than the lethal concentration on mutated cell(s), still more preferably, the lethal concentration on naive cell(s) is 1000-fold lower than the lethal concentration on mutated cell(s).

The herbicide (used in the method of the present invention) can be a mixture (of inhibitors) comprising at least one ALS inhibitor, such as foramsulfuron.

Possibly, the ALS inhibitor used in the method of the invention is a mixture of ALS inhibitors, such as a sulfonylurea (e.g. foramsulfuron) and another ALS inhibitor selected from the group consisting of iodosulfuron, amidosulfuron and thiencarbazone-methyl.

Preferably, the ALS inhibitor used in the method of the invention is (or comprises) foramsulfuron, such as foramsulfuron applied to a one-week old (or to a three-weeks old) in vitro culture of protoplasts (more particularly to the in vitro culture comprising calli regenerated from these cultured protoplasts) on alginate-containing medium and maintained during the in vitro culture of the cells at a concentration of $10^{-9}$-$10^{-6}$ mol/l (or $10^{-9}$-$10^{-6}$ mol/l).

A related aspect of the present invention is a mutated sugar beet plant obtainable by this method, (for instance when this methods comprises the use of one or more herbicide (not ALS inhibitors) or the use of one or more ALS inhibitors, or comprises the use of one ALS inhibitor and of one herbicide being not an ALS inhibitor).

Therefore, one aspect of the present invention is a sugar beet (obtainable by the method of the present invention) having one or several mutation(s) in the ALS gene at positions encoding the amino acids selected from the group consisting of Glycine 112, Alanine 113, Methionine 115, Arginine 133, Valine 187, Arginine 190, Alanine 196, Phenylalanine 197, Lysine 247, Methionine 346, Histidine 347, Arginine 368, Aspartate 370, Aspartate 371, Arginine 372, Methionine 565, Valine 566, Phenylalanine 573, Serine 648 and Glycine 649.

A preferred sugar beet (obtainable by the method of the present invention) has one or several mutation(s) in the ALS gene at positions encoding the amino acids selected from the group consisting of Alanine 113 (e.g. mutated into Valine or Threonine) Proline 188 mutated into Threonine, Arginine, Leucine, Glutamine or Alanine, Alanine 196 (e.g. mutated into Valine), Aspartate 371 (e.g. mutated into glutamate), Arginine 372 (e.g. mutated into Histidine), Tryptophan 569 mutated into Glycine, Serine 648 (e.g. mutated into Threonine) and Glycine 649 (e.g. mutated into Aspartate).

A related aspect of the present invention is a mutated sugar beet plant (or a mutated sugar beet plant cell such as a mutated stomatal guard cell isolated from sugar beet) comprising a mutation in the ALS gene where the tryptophan at position 569 in the encoded ALS enzyme (corresponding to position 574 in the *Arabidopsis thaliana* ALS enzyme) is substituted by another amino acid (such as a leucine), and possibly another (one or several) mutation, preferably another (one or several) mutation in the ALS gene, such as a mutation causing a further amino acid substitution in the ALS gene.

Another preferred a sugar beet plant has a mutation of the Tryptophan into Leucine at position 569 and one or several mutation(s) in the ALS gene at positions encoding the amino acids selected from the group consisting of Glycine 112, Alanine 113, Methionine 115, Arginine 133, Valine 187, Arginine 190, Alanine 196, Phenylalanine 197, Lysine 247, Methionine 346, Histidine 347, Arginine 368, Aspartate 370, Aspartate 371, Arginine 372, Methionine 565, Valine 566, Phenylalanine 573, Serine 648 and Glycine 649.

A preferred sugar beet (obtainable by the method of the present invention) has one mutation Tryptophan into Leucine mutation at position 569 and one or several mutation(s) in the ALS gene at positions encoding the amino acids selected from the group consisting of Alanine 113 (e.g. mutated into Valine or Threonine) Proline 188 mutated into Threonine, Arginine, Leucine, Glutamine or Alanine, Alanine 196 (e.g. mutated into Valine), Aspartate 371 (e.g. mutated into Glutamate), Arginine 372 (e.g. mutated into Histidine), Serine 648 (e.g. mutated into Threonine) and Glycine 649 (e.g. mutated into Aspartate).

This mutated sugar beet plant is resistant to one or several ALS inhibitor(s) used, such as a sulfonylurea (e.g. foramsulfuron) and advantageously to other ALS inhibitor(s), preferably selected from the group consisting of iodosulfuron, amidosulfuron and thiencarbazone-methyl.

A related aspect of the present invention is a mutated sugar beet plant (or a mutated sugar beet plant cell such as a mutated stomatal guard cell isolated from sugar beet) comprising a mutation in the ALS gene where the proline at position 188 in the encoded ALS enzyme (corresponding to position 197 in *Arabidopsis thaliana* ALS enzyme) is substituted by another amino acid (such as a serine).

Alternatively, a preferred sugar beet plant (obtainable by the method of the present invention) has a mutation of the Proline into Serine at position 188 and one or several mutation(s) in the ALS gene at positions encoding the amino acids selected from the group consisting of Glycine 112, Alanine 113, Methionine 115, Arginine 133, Valine 187, Arginine 190, Alanine 196, Phenylalanine 197, Lysine 247, Methionine 346, Histidine 347, Arginine 368, Aspartate 370, Aspartate 371, Arginine 372, Methionine 565, Valine 566, Phenylalanine 573, Serine 648 and Glycine 649.

A preferred sugar beet (obtainable by the method of the present invention) has one Proline into Serine mutation in the ALS gene at position 188 and one or more mutation(s) of the ALS gene at positions encoding Alanine 113 (e.g. mutated into Valine or Threonine), Aspartate 371 (e.g. mutated into glutamate), Arginine 372 (e.g. mutated into Histidine), Tryptophan 569 mutated into Glycine, Serine 648 (e.g. mutated into Threonine) and Glycine 649 (e.g. mutated into Aspartate).

Another related aspect of the present invention is a mutated sugar beet plant (or a mutated sugar beet plant cell such as a mutated stomatal guard cell isolated from sugar beet) comprising a mutation of tryptophan at position 569 in the ALS enzyme and a mutation of proline at position 188 in the ALS enzyme, as well as possibly another (one or several) mutation, preferably another (one or several) mutation in the ALS gene.

Preferably, (one allele of) the ALS gene of this mutated sugar beet plant corresponds to SEQ.ID.NO:3 or SEQ.ID.NO:5.

Advantageously, the mutated sugar beet plant of the present invention comprises SEQ.ID.NO:3 (in one allele) and SEQ.ID.NO:5 (in the second allele).

Possibly, the mutated sugar beet plant of the present invention comprises SEQ.ID.NO:3 (in one allele) and either SEQ.ID.NO:1, or SEQ.ID.NO:7 (in the second allele).

Another related aspect of the present invention is a nucleotide fragment (of at least 20 or at least 25 consecutive nucleotides, but of less than 200 consecutive nucleotides, preferably of less than 50 consecutive nucleotides) covering the one or more mutations; possibly this fragment is for use as a primer or a probe (including a nucleotide probe being further labelled e.g. by a non-nucleotidic moiety or using radioactivity, or a probe labelled with a nucleic acid sequence foreign to the ALS gene of sugar beet).

Still another related aspect of the present invention is the use of this nucleotide fragment spanning over the mutation for marker-assisted selection of sugar beet plants having a resistance towards the toxic molecule (herbicide).

EXAMPLES

Comparative Example

Because mutated sugar beet were successfully generated in the art (e.g. in WO 98/02527) upon the addition of ALS herbicide to calli being explants from wild-type sugar beet, the inventors firstly selected the sugar beet genotype (line) derived from the line of WO 98/02527 and isolated protoplasts from their stomatal guard cells.

Several millions of these protoplasts (on average about 2 to about 5 millions, and up to 11 millions by experiment; in total, ALS herbicide was applied to about 150 millions of protoplasts) were isolated as in WO 95/10178, placed in culture medium comprising alginate, and treated with MS culture medium comprising $10^{-9}$ to $10^{-6}$ mol/l foramsulfuron.

The inventors have then regenerated the sugar beet, following the protocol as described in WO 95/10178, and observed only a few calli surviving to the ALS inhibitor. However, to one exception, none of these regenerated calli were able to develop into a sugar beet plant. The only regenerated sugar beet plant showed no mutation in the ALS gene (encoding the target enzyme of foramsulfuron).

Therefore this sugar beet line, whose parental line was shown, on the basis of the direct exposition of calli (from an explant) to an herbicide, to acquire mutation-induced resistance to this herbicide, was not useful for the same purpose, when the method involves stomatal guard cells protoplasts.

Example 1 Selection of Sugar Beet Genotypes (Lines) for Well-Regenerating Protoplasts The inventors have then compared several sugar beet plant genotypes for their capacity of regeneration from stomatal guard cells protoplasts.

The inventors have found genotypes having about 0.01% (or even less) of capacity to regenerate and several genotypes having (much) more than 0.1% of capacity to regenerate.

The inventors have further established a distinction between the growth of the protoplasts (their capacity to growth and divide in vitro), the capacity of the grown calli to form shoots and the proportion of growing calli to regenerate a plant.

TABLE 1 comparison of some sugar beet genotypes

| Genotype | Protoplasts/ gram | Percentage growing cells (%) | Percentage shoot formation (%) | Percentage obtained plants (%) |
|---|---|---|---|---|
| F06R38309 | 1500000 | 0.02 | 55.67 | 3.43 |
| F06R38313 | 500000 | 0.04 | 0.14 | 0.00 |
| F06R38323 | 1000000 | 0.19 | 0.49 | 10.81 |
| F07R38836 | 500000 | 0.26 | 10.51 | 0.73 |
| REL1 | 1000000 | 0.07 | 70.00 | 44.00 |

Although the values reflecting the capacity of a stomatal guard cell protoplast to regenerate into a whole sugar beet plant, when taken as a whole were higher for the cell line "Rel1", this cell line was considered as not useful enough for running the present invention.

The inventors have further concluded that the "percentage of growing cells" parameter is much more important for running the present invention than the other parameters.

The inventors have selected a genotype having more than 0.25% of stomatal guard cells protoplasts that are able to grow in vitro.

Example 2 Herbicide Treatment of Protoplasts

The inventors have applied the same approach as in the comparative Example, but relying on well growing stomatal guard cells protoplasts (for instance identified as in Example 1; plants deposited as NCIMB 42050 or NCIMB 42051 can also be used, as well as other sugar beet plants having a high proportion of growing stomatal guard cell protoplasts).

In total, about 68 millions of well-growing stomatal guard cell protoplasts were treated with an ALS herbicide composition comprising up to $10^{-6}$M foramsulfuron.

The inventors obtained 46 calli.

Several regenerated plants are showing a mutation in the target gene, the ALS gene: in each case a mutation in the codon for tryptophan at position 569 (W569L; corresponding to tryptophan at position 574 in *Arabidopsis thaliana*). The two alleles of the ALS genes of this mutant are encoded by SEQ.ID.NO:3 and SEQ.ID.NO:7. Other grown calli were sequenced and have mutations in the ALS gene, (including mutations at other positions) but did not regenerate into a plant.

The inventors therefore conclude that the method of the present invention is very useful to develop plants having evolved mutations causing a resistance to an herbicide, especially since this method does not involve the use of foreign DNA and/or the introduction of DNA vectors encoding genetic elements already known to confer resistance to ALS inhibitors, and yielded positive results in only a few months.

The inventors then repeated this method and further applied a mutagen (0.05% to 0.2% EMS) to the protoplasts in order to increase the number of mutations.

Example 3 ALS Inhibitor Treatment of Sugar Beets

The inventors compared the behaviour of regenerated sugar beets having the mutated SEQ.ID.NO:3 (heterozygote for this mutation) and a wild-type (naive) sugar beet commercial variety.

The (heterozygote) mutated variety showed good resistance to Foramsulfuron (12.5 g/ha; up to 3 applications), even when the herbicide has been combined with an organic compound (25 g/ha rapeseed oil methyl ester) to boost its effect.

As expected, the wild-type (naive) plant was very sensitive to Foramsulfuron, even after the first application.

The same experiment was performed using amidosulfuron (15 g/ha), and yielded the same level of resistance in the mutated plants.

On the other hand, the wild-type (naive) plants were very sensitive to amidosulfuron, especially when combined with the organic compound, and/or after several applications of amidosulfuron.

The same experiment was performed using iodosulfuron (3.5 g/ha), and demonstrated a good level of resistance in the mutated plants when iodosulfuron was added, but this resistance declined when iodosulfuron is applied together with the organic compound. As expected, the wild-type (naive) plant was very sensitive to iodosulfuron even after one application and without the organic compound.

The same experiment was performed using 7.5 g/ha thiencarbazone-methyl, and yielded about the same level of resistance as for iodosulfuron in the mutated plants. The wild-type (naive) plant was very sensitive to thiencarbazone-methyl at all the tested concentrations and regardless of the addition of the organic compound.

The inventors conclude that, by comparison to the wild-type, the mutated sugar beet plant comprising SEQ.ID.NO:3 (deposited under the Budapest Treaty NCIMB 42051) offers the best resistance against foramsulfuron.

The inventors further conclude that this (heterozygote) mutated plant has further acquired some (although partial) resistance towards other ALS inhibitors, including towards inhibitors belonging to other chemical classes.

Example 4 ALS Inhibitor Treatment of Sugar Beets Having Further Mutations in the ALS Gene The inventors then developed a mutated sugar beet plant comprising SEQ.ID.NO:3 and SEQ.ID.NO:5 (on two different alleles). Such resulting dual mutant has been deposited under the Budapest Treaty under NCIMB 42050. A plant comprising both SEQ.ID.NO:3 and SEQ.ID.NO:5 can be generated by relying on several techniques, including, for instance, a subsequent mutagenesis step applied to the single mutant NCIMB 42051.

The inventors then compared the resistance of this dual mutant plant (a mutation in one allele at amino acid 569 and a mutation in the other allele at amino acid 188) with the single mutant (a mutation at position 569) sugar beet.

The dual mutant plant line at least keeps all the resistance features as in Example 3, and has also acquired a good resistance (compatible with field application) towards thiencarbazone-methyl and towards amidosulfuron treatments, even when put in composition with organic compounds.

Therefore, this dual mutant plant displays improved, synergistic, resistance towards several ALS inhibitors by comparison to the resistance attributed to the single mutant plant (at position 569 in the ALS gene).

Example 5 Greenhouse Trials: ALS Inhibitor Treatment of Different Sugar Beets in Direct Comparison Mutated sugar beet plants comprising SEQ.ID.NO:3 and SEQ.ID.NO:5 (on two different alleles) according to the present invention (as described in Example 4 above, "Line A") were treated with different ALS inhibitors in direct comparison with sugar beet plants where the tryptophan at position 569 of the encoded ALS enzyme is substituted by a leucine ("Line B"), sugar beet plants described in WO 98/02527 where the proline at position 188 of the encoded ALS enzyme is substituted by a serine ("Line C"), and traditional variety (wild-type) sugar beet plants not having a mutation at positions 569 and 188 ("Line WT").

Several groups of seeds of the four different mentioned sugar beet plants were sown separately in the greenhouse and grew up to stage BBCH 14 for *Beta vulgaris* L. ssp. vulgaris (i.e. 4 leaves (the second pair) unfolded) according to the monographie "Entwicklungsstadien mono-und dikotyler Pflanzen", $2^{nd}$ edition, 2001, ed. Uwe Meier, Biologische Bundesanstalt für Land und Forstwirtschaft. Subsequently, the resulting separate groups of sugar beet plants were each individually treated with an ALS inhibitor (ALS-in) in the amounts (g/ha) indicated in Table 2.

On day 14 after application of the respective ALS inhibitor, the damage (i.e. the phytotoxicity) for each sugar beet plant was rated on a scale from 0% (i.e. no damage, no phytotoxicity) to 100% (i.e. the plants were completely killed). The average rating for each group of plants is also shown in Table 2.

TABLE 2

| ALS-in | ALS-in g/ha | Line A | Line B | Line C | Line WT |
|---|---|---|---|---|---|
| Foramsulfuron | 13 | 26.9% | 45.6% | 77.5% | 80.0% |
| Iodosulfuron-methyl-Na | 3.5 | 22.5% | 38.8% | 80.0% | 82.5% |
| Amidosulfuron | 15 | 6.3% | 37.5% | 51.9% | 73.1% |
| Thiencarbazone-methyl | 7.5 | 8.1% | 35.6% | 37.5% | 84.4% |
| Bisbyribac-Na | 50 | 17.5% | 38.1% | 71.7% | 80.0% |
| Metosulam | 15 | 13.1% | 40.6% | 69.4% | 79.4% |

Additionally, typical early phenotypes of each sugar beet plants were inspected after treatment with a mixture comprising thiencarbazone-methyl and foramsulfuron. A representative early phenotype of each Line is shown in FIG. 1 (FIG. 1).

FIG. 1 also demonstrates that the sugar beet plants according to the present invention ("Line A") show improved ALS inhibitor resistance, i.e. superior growth and less phytotoxic effects were observed in comparison to the other early phenotypes.

Example 6 Field Trials: ALS Inhibitor Treatment of Different Sugar Beets in Direct Comparison

TABLE 3

Table 3: effect of ALS inhibitors on sugar beet plant. The values represent the average percentage of measured damage.

| | | Sensitive | 574 hetero | 574&197 | 574 homo |
|---|---|---|---|---|---|
| 1 | UNTREATED | 0 | 0 | 0 | 0 |
| 2 | AE F 130360 00 WG50 A1 25 g/HA (Foramsulfuron) | 97 | 22 | 5 | 0 |
| 3 | BYH18636 15 g/Ha (Thiencarbazone) | 97 | 39 | 5 | 0 |
| 4 | ae f115008 00 wg 10 a2 7 g/Ha (iodosulfuron) | 98 | 65 | 23 | 28 |
| 5 | AE F130060 00 WG75 A2 60 g/Ha (mesosulfuron) | 91 | 24 | 18 | 0 |
| 6 | HOESTAR 30 g/Ha (amidosulfuron) | 97 | 34 | 0 | 0 |
| 7 | AEF095404 00 WG60 A2 60 g/Ha (ethoxysulfuron) | 99 | 39 | 0 | 0 |
| 8 | RAPTOR 40 g/Ha (imazamox) | 98 | 44 | 35 | 8 |
| 9 | TACCO 30 g/Ha (metosulam) | 97 | 27 | 0 | 3 |
| 10 | NOMINEE 50 g/Ha (bispyribac) | 98 | 78 | 70 | 28 |
| 11 | MOTIVELL 60 g/Ha (nicosulfuron) | 98 | 53 | 28 | 13 |
| 12 | GROPPER SX 8 g/Ha (metosulfuron) | 100 | 74 | 50 | 35 |
| 13 | LEXUS 50 DF 10 g/Ha (flupyrsulfuron) | 70 | 0 | 0 | 0 |
| 14 | ATTRIBUT 70 g/Ha (propoxycarabazone) | 91 | 25 | 0 | 5 |
| 15 | SIMPLICITY 50 g/Ha (pyroxysulam) | 97 | 45 | 28 | 0 |
| 16 | PRIMUS 10 g/Ha (florasulam) | 99 | 55 | 38 | 0 |
| 17 | POINTER SX 30 g/Ha (tribenuron) | 98 | 74 | 28 | 20 |
| 18 | CATO 13 g/Ha (rimsulfuron) | 68 | 8 | 0 | 0 |
| 19 | MONITOR 80 WG 10 g/Ha (sulfosulfuron) | 93 | 23 | 0 | 0 |
| 20 | DEBUT YX1 15 g/Ha (triflusulfuron) | 0 | 0 | 0 | 0 |
| 21 | EVEREST 40 g/Ha (flucarbazone) | 93 | 18 | 0 | 0 |
| 22 | HARMONY 7.5 g/Ha (thiensulfuron) | 98 | 39 | 0 | 0 |
| 23 | #2 & #3 (Foramsulfuron + Thiencarbazone) 1 L/Ha | 100 | 65 | 35 | 5 |

The inventors have tested commercial compositions at the dose allowing destruction of the weeds.

The sensitive control (i.e. a sugar beet having no mutation in the ALS gene) was killed by all the herbicides but one. The inventors have measured small damages to control (untreated) plant, reaching sometimes 35% or even 40%. These 'damages' reflect the agronomic conditions of this field trial.

On the other hand, sugar beet plant being heterozygote at position 569 (574) have become partially resistant towards several herbicidal compositions. The plant having incorporated the 569 mutation (574) on both alleles and thus being (569/569) homozygote has a further increased resistance: only 7 herbicide composition are moderately toxic (from 5% to 35%).

A sugar beet plant having incorporated the mutation at position 569 (574) in one allele of the ALS gene and a mutation at position 188 (197) in the second allele of the ALS gene have also acquired improved resistance, since 9 herbicide compositions are moderately toxic, and only 3 are quite toxic. Surprisingly, such plant, where a mutation providing a strong resistance (569) has been lost and a mutation providing only a weak resistance (188) towards ALS inhibitor has been added, provides even better resistance than the homozygote (569/569) plant in 3 different conditions of this field test.

The invention claimed is:

1. A method for producing a mutant sugar beet plant resistant to one or more inhibitor(s) of the acetohydroxyacid synthase enzyme (ALS) comprising the steps of:

comparing a plurality of different sugar beet plant genotypes for the capacity of their stomatal guard cells protoplasts to regenerate into a sugar beet plant;

selecting one of the plurality of different sugar beet plant genotypes having stomatal guard cells protoplasts with a probability of more than 10% to regenerate into viable sugar beet callus and more than 10% of calli obtained by said protoplasts having a capacity to develop shoots, wherein the one of the plurality of different sugar beet plant genotypes comprises the 4D genotype sugar beet plant, wherein a representative sample of the 4D genotype sugar beet seed has been deposited under NCIMB 43423;

obtaining protoplasts from stomatal guard cells isolated from a sugar beet plant of the selected genotype;

applying to an in vitro culture of more than 20,000,000 of said protoplasts a composition comprising one or more ALS inhibitor(s) at a concentration that is lethal to more than 99% of the in vitro cultured cells; and regenerating a sugar beet plant from the surviving cells of said in vitro cultured cells, wherein the regenerated sugar beet plant is a mutant sugar beet plant resistant to one or more ALS inhibitor(s).

2. The method of claim 1, wherein the step of comparing comprises the sub-steps of isolating stomatal guard cells protoplasts from sugar beet plants of different genotypes and measuring for each genotype the proportion of said protoplasts that is growing when said protoplasts are put into in vitro culture.

3. The method of claim 1 further comprising the step of sequencing the genome of the regenerated plants from the surviving in vitro cultured cells.

4. The method according to claim 1 further comprising the step of sequencing the ALS gene for identifying a mutation in the ALS gene.

5. The method according to claim 1 further comprising the step of selecting regenerated sugar beet plants having a mutation in the ALS gene.

6. The method according to claim 3 wherein the regenerated sugar beet plant has one or several mutation(s) in the ALS gene at positions encoding the amino acids selected from the group consisting of Glycine 112, Alanine 113, Methionine 115, Arginine 133, Valine 187, Arginine 190, Alanine 196, Phenylalanine 197, Lysine 247, Methionine 346, Histidine 347, Arginine 368, Aspartate 370, Aspartate 371, Arginine 372, Methionine 565, Valine 566, Phenylalanine 573, Serine 648 and Glycine 649, wherein the amino acid numbering corresponds to the amino acid sequence set forth in SEQ ID NO: 2.

7. The method according to claim 3, wherein the regenerated sugar beet plant has one mutation in the ALS gene at positions encoding proline 188 and one or more mutation(s) in the ALS gene at positions encoding Glycine 112, Alanine 113, Methionine 115, Arginine 133, Valine 187, Arginine 190, Alanine 196, Phenylalanine 197, Lysine 247, Methionine 346, Histidine 347, Arginine 368, Aspartate 370, Aspartate 371, Arginine 372, Methionine 565, Valine 566, Tryptophan 569, Phenylalanine 573, Serine 648 and Glycine 649, wherein the amino acid numbering corresponds to the amino acid sequence set forth in SEQ ID NO: 2.

8. The method according to claim 3, wherein the regenerated sugar beet plant has one mutation in the ALS gene at positions encoding tryptophan 569 and one or more mutation(s) in the ALS gene at positions encoding Glycine 112, Alanine 113, Methionine 115, Arginine 133, Valine 187, Proline 188, Arginine 190, Alanine 196, Phenylalanine 197, Lysine 247, Methionine 346, Histidine 347, Arginine 368, Aspartate 370, Aspartate 371, Arginine 372, Methionine 565, Valine 566, Phenylalanine 573, Serine 648 and Glycine 649, wherein the amino acid numbering corresponds to the amino acid sequence set forth in SEQ ID NO: 2.

9. The method according to claim 3, wherein the regenerated sugar beet plant has one or more mutation(s) in the ALS gene, wherein said one or more mutation is selected from the group consisting of Alanine 113, Proline 188, Alanine 196, Aspartate 371, Arginine 372, Tryptophan 569, Serine 648 and Glycine 649, wherein said Alanine 113 is mutated into Valine or Threonine, wherein said Proline 188 is mutated into Threonine, Arginine, Leucine, Glutamine or Alanine, wherein said Alanine 196 is mutated into Valine, wherein said Aspartate 371 is mutated into Glutamate, wherein said Arginine 372 is mutated into Histidine, wherein said Tryptophan 569 is mutated into Glycine, wherein said Serine 648 is mutated into Threonine and wherein said and Glycine 649 is mutated into Aspartate, wherein the amino acid numbering corresponds to the amino acid sequence set forth in SEQ ID NO: 2.

10. The method according to claim 3, wherein the regenerated sugar beet plant has one mutation in the ALS gene at position encoding Proline 188 and one mutation in the ALS gene at position encoding Tryptophan 569, wherein the amino acid numbering corresponds to the amino acid sequence set forth in SEQ ID NO: 2.

11. The method according to claim 1 comprising a preliminary step of deducing the concentration at which the composition comprising the one or more ALS inhibitor(s) is/are lethal for at least 99% of the in vitro cultured cells.

12. The method according to claim 1 wherein the one or more ALS inhibitor(s) is/are applied to an in vitro culture of more than 50,000,000 of stomatal guard cell protoplasts.

13. The method according to claim 1, wherein the composition comprising one or more ALS inhibitor(s) comprises foramsulfuron.

14. The method of claim 13, wherein the foramsulfuron is applied at a concentration in the range of $10^{-9}$ mol/l to $10^{-6}$ mol/l.

15. The method according to claim 1, wherein the composition comprising one or more ALS inhibitor(s) comprises ethoxysulfuron.

16. A method for producing a mutant sugar beet plant being resistant to an herbicide comprising the steps of:
comparing a plurality of different sugar beet plant genotypes for the capacity of their stomatal guard cells protoplasts to regenerate into a sugar beet plant;
selecting one of the plurality of different sugar beet plant genotypes having stomatal guard cells protoplasts with a probability of more than 10% to regenerate into viable sugar beet callus and more than 10% of calli obtained by said protoplasts having a capacity to develop shoots, the one of the plurality of different sugar beet plant genotypes is the 4D genotype sugar beet plant or a sugar beet plant having the same regenerating properties as the 4D genotype, wherein a representative sample of the 4D genotype sugar beet seed has been deposited under NCIMB 43423;
obtaining protoplasts from stomatal guard cells isolated from a sugar beet plant of the selected genotype;
applying to an in vitro culture of more than 20,000,000 of said protoplasts a composition comprising said herbicide at a concentration that is lethal to more than 99% of the in vitro cultured cells;
regenerating sugar beet plants from the surviving cells of said in vitro cultured cells; and
selecting regenerated sugar beet plants having a mutation in the gene encoding the peptide targeted by said herbicide.

17. The method of claim 16, wherein the herbicide is selected from the group consisting of 4-HPPD inhibitors, inhibitors of the carotenoid biosynthesis, inhibitors of EPSP synthase, inhibitors of phosphosystem II, inhibitors of phosphosystem I, inhibitors of cell division, inhibitors of microtubule assembly, inhibitors of protoporphyrinogen oxidase, inhibitors of Acetyl CoA carboxylase, cell wall synthesis inhibitors, inhibitor of glutamine synthetase and synthetic auxin.

18. Stomatal guard cell protoplasts isolated from the mutant sugar beet plant of claim 1.

19. A method of modifying the stomatal guard cell protoplasts of claim 18 comprising introducing one or more further genetic traits into the protoplasts.

20. The method of claim 1, wherein the one of the plurality of different sugar beet plant genotypes is the 4D genotype sugar beet plant or a mutant of the 4D genotype having all of the morphological and physiological properties of 4D, wherein a representative sample of the 4D genotype sugar beet seed has been deposited under NCIMB 43423.

21. The method of claim 16, wherein the one of the plurality of different sugar beet plant genotypes is the 4D genotype sugar beet plant, wherein a representative sample of the 4D genotype sugar beet seed has been deposited under NCIMB 43423.

* * * * *

```
                        SEQUENCE LISTING

<160> NUMBER OF SEQ ID NOS: 8

<210> SEQ ID NO 1
<211> LENGTH: 1998
<212> TYPE: DNA
<213> ORGANISM: Beta Vulgaris
<220> FEATURE:
<221> NAME/KEY: CDS
<222> LOCATION: (1)..(1998)
<223> OTHER INFORMATION: 4D6834 WT all

<400> SEQUENCE: 1 atg gcg gct acc ttc aca aac cca aca ttt tcc cct tcc tca act cca       48
Met Ala Ala Thr Phe Thr Asn Pro Thr Phe Ser Pro Ser Ser Thr Pro
1               5                   10                  15 tta acc aaa acc cta aaa tcc caa tct tcc atc tct tca acc ctc ccc       96
Leu Thr Lys Thr Leu Lys Ser Gln Ser Ser Ile Ser Ser Thr Leu Pro
            20                  25                  30
```

| | | |
|---|---|---|
| ttt tcc acc cct ccc aaa acc cca act cca ctc ttt cac cgt ccc ctc<br>Phe Ser Thr Pro Pro Lys Thr Pro Thr Pro Leu Phe His Arg Pro Leu<br>35 40 45 | 144 | |
| caa atc tca tcc tcc caa tcc cac aaa tca tcc gcc att aaa aca caa<br>Gln Ile Ser Ser Ser Gln Ser His Lys Ser Ser Ala Ile Lys Thr Gln<br>50 55 60 | 192 | |
| act caa gca cct tct tct cca gct att gaa gat tca tct ttc gtt tct<br>Thr Gln Ala Pro Ser Ser Pro Ala Ile Glu Asp Ser Ser Phe Val Ser<br>65 70 75 80 | 240 | |
| cga ttt ggc cct gat gaa ccc aga aaa ggg tcc gat gtc ctc gtt gaa<br>Arg Phe Gly Pro Asp Glu Pro Arg Lys Gly Ser Asp Val Leu Val Glu<br>85 90 95 | 288 | |
| gct ctt gag cgt gaa ggt gtt acc aat gtg ttt gct tac cct ggt ggt<br>Ala Leu Glu Arg Glu Gly Val Thr Asn Val Phe Ala Tyr Pro Gly Gly<br>100 105 110 | 336 | |
| gca tct atg gaa atc cac caa gct ctc aca cgc tct aaa acc atc cgc<br>Ala Ser Met Glu Ile His Gln Ala Leu Thr Arg Ser Lys Thr Ile Arg<br>115 120 125 | 384 | |
| aat gtc ctc cct cgc cat gaa caa ggc ggg gtt ttc gcc gcc gag gga<br>Asn Val Leu Pro Arg His Glu Gln Gly Gly Val Phe Ala Ala Glu Gly<br>130 135 140 | 432 | |
| tat gct aga gct act gga aag gtt ggt gtc tgc att gcg act tct ggt<br>Tyr Ala Arg Ala Thr Gly Lys Val Gly Val Cys Ile Ala Thr Ser Gly<br>145 150 155 160 | 480 | |
| cct ggt gct acc aac ctc gta tca ggt ctt gct gac gct ctc ctt gat<br>Pro Gly Ala Thr Asn Leu Val Ser Gly Leu Ala Asp Ala Leu Leu Asp<br>165 170 175 | 528 | |
| tct gtc cct ctt gtt gcc atc act ggc caa gtt cca cgc cgt atg att<br>Ser Val Pro Leu Val Ala Ile Thr Gly Gln Val Pro Arg Arg Met Ile<br>180 185 190 | 576 | |
| ggc act gat gct ttt cag gag act cca att gtt gag gtg aca agg tct<br>Gly Thr Asp Ala Phe Gln Glu Thr Pro Ile Val Glu Val Thr Arg Ser<br>195 200 205 | 624 | |
| att act aag cat aat tat tta gtt ttg gat gta gag gat att cct aga<br>Ile Thr Lys His Asn Tyr Leu Val Leu Asp Val Glu Asp Ile Pro Arg<br>210 215 220 | 672 | |
| att gtt aag gaa gcc ttt ttt tta gct aat tct ggt agg cct gga cct<br>Ile Val Lys Glu Ala Phe Phe Leu Ala Asn Ser Gly Arg Pro Gly Pro<br>225 230 235 240 | 720 | |
| gtt ttg att gat ctt cct aaa gat att cag cag caa ttg gtt gtt cct<br>Val Leu Ile Asp Leu Pro Lys Asp Ile Gln Gln Gln Leu Val Val Pro<br>245 250 255 | 768 | |
| gat tgg gat agg cct ttt aag ttg ggt ggg tat atg tct agg ctg cca<br>Asp Trp Asp Arg Pro Phe Lys Leu Gly Gly Tyr Met Ser Arg Leu Pro<br>260 265 270 | 816 | |
| aag tcc aag ttt tcg acg aat gag gtt gga ctt ctt gag cag att gtg<br>Lys Ser Lys Phe Ser Thr Asn Glu Val Gly Leu Leu Glu Gln Ile Val<br>275 280 285 | 864 | |
| agg ttg atg agt gag tcg aag aag cct gtc ttg tat gtg gga ggt ggg<br>Arg Leu Met Ser Glu Ser Lys Lys Pro Val Leu Tyr Val Gly Gly Gly<br>290 295 300 | 912 | |
| tgt ttg aat tct agt gag gag ttg agg aga ttt gtt gag ttg aca ggg<br>Cys Leu Asn Ser Ser Glu Glu Leu Arg Arg Phe Val Glu Leu Thr Gly<br>305 310 315 320 | 960 | |
| att ccg gtg gct agt act ttg atg ggg ttg ggg tct tac cct tgt aat<br>Ile Pro Val Ala Ser Thr Leu Met Gly Leu Gly Ser Tyr Pro Cys Asn<br>325 330 335 | 1008 | |
| gat gaa ctg tct ctt cat atg ttg ggg atg cac ggg act gtt tat gcc<br>Asp Glu Leu Ser Leu His Met Leu Gly Met His Gly Thr Val Tyr Ala<br>340 345 350 | 1056 | |

```
aat tat gcg gtg gat aag gcg gat ttg ttg ctt gct ttc ggg gtt agg      1104
Asn Tyr Ala Val Asp Lys Ala Asp Leu Leu Leu Ala Phe Gly Val Arg
        355                 360                 365 ttt gat gat cgt gtg acc ggg aag ctc gag gcg ttt gct agc cgt gct      1152
Phe Asp Asp Arg Val Thr Gly Lys Leu Glu Ala Phe Ala Ser Arg Ala
370                 375                 380 aag att gtg cat att gat att gac tct gct gag att ggg aag aac aag      1200
Lys Ile Val His Ile Asp Ile Asp Ser Ala Glu Ile Gly Lys Asn Lys
385                 390                 395                 400 cag ccc cat gtg tcc att tgt gct gat gtt aaa ttg gca ttg cgg ggt      1248
Gln Pro His Val Ser Ile Cys Ala Asp Val Lys Leu Ala Leu Arg Gly
            405                 410                 415 atg aat aag att ctg gag tct aga ata ggg aag ctg aat ttg gat ttc      1296
Met Asn Lys Ile Leu Glu Ser Arg Ile Gly Lys Leu Asn Leu Asp Phe
        420                 425                 430 tcc aag tgg aga gaa gaa tta ggt gag cag aag aag gaa ttc cca ctg      1344
Ser Lys Trp Arg Glu Glu Leu Gly Glu Gln Lys Lys Glu Phe Pro Leu
    435                 440                 445 agt ttt aag aca ttt ggg gat gca att cct cca caa tat gcc att cag      1392
Ser Phe Lys Thr Phe Gly Asp Ala Ile Pro Pro Gln Tyr Ala Ile Gln
450                 455                 460 gtg ctt gat gag ttg acc aat ggt aat gct att ata agt act ggt gtt      1440
Val Leu Asp Glu Leu Thr Asn Gly Asn Ala Ile Ile Ser Thr Gly Val
465                 470                 475                 480 ggg cag cac caa atg tgg gct gcg cag cat tac aag tac aga aac cct      1488
Gly Gln His Gln Met Trp Ala Ala Gln His Tyr Lys Tyr Arg Asn Pro
            485                 490                 495 cgc caa tgg ctg acc tct ggt ggg ttg ggg gct atg ggg ttt ggg cta      1536
Arg Gln Trp Leu Thr Ser Gly Gly Leu Gly Ala Met Gly Phe Gly Leu
        500                 505                 510 cca gcc gcc att gga gct gca gtt gct cga cca gat gca gtg gtt gtc      1584
Pro Ala Ala Ile Gly Ala Ala Val Ala Arg Pro Asp Ala Val Val Val
    515                 520                 525 gat att gat ggg gat ggc agt ttt att atg aat gtt caa gag ttg gct      1632
Asp Ile Asp Gly Asp Gly Ser Phe Ile Met Asn Val Gln Glu Leu Ala
530                 535                 540 aca att agg gtg gaa aat ctc cca gtt aag ata atg ctg cta aac aat      1680
Thr Ile Arg Val Glu Asn Leu Pro Val Lys Ile Met Leu Leu Asn Asn
545                 550                 555                 560 caa cat tta ggt atg gtt gtc caa tgg gaa gat agg ttc tat aaa gct      1728
Gln His Leu Gly Met Val Val Gln Trp Glu Asp Arg Phe Tyr Lys Ala
            565                 570                 575 aac cgg gca cat aca tac ctt gga aac cct tcc aaa tct gct gat atc      1776
Asn Arg Ala His Thr Tyr Leu Gly Asn Pro Ser Lys Ser Ala Asp Ile
        580                 585                 590 ttc cct gat atg ctc aaa ttc gct gag gca tgt gat att cct tct gcc      1824
Phe Pro Asp Met Leu Lys Phe Ala Glu Ala Cys Asp Ile Pro Ser Ala
    595                 600                 605 cgt gtt agc aac gtg gct gat ttg agg gcc gcc att caa aca atg ttg      1872
Arg Val Ser Asn Val Ala Asp Leu Arg Ala Ala Ile Gln Thr Met Leu
610                 615                 620 gat act cca ggg ccg tac ctg ctc gat gtg att gta ccg cat caa gag      1920
Asp Thr Pro Gly Pro Tyr Leu Leu Asp Val Ile Val Pro His Gln Glu
625                 630                 635                 640 cat gtg ttg cct atg att cca agt ggt gcc ggt ttc aag gat acc att      1968
His Val Leu Pro Met Ile Pro Ser Gly Ala Gly Phe Lys Asp Thr Ile
            645                 650                 655 aca gag ggt gat gga aga acc tct tat tga                              1998
Thr Glu Gly Asp Gly Arg Thr Ser Tyr
```

<210> SEQ ID NO 2
<211> LENGTH: 665
<212> TYPE: PRT
<213> ORGANISM: Beta Vulgaris

<400> SEQUENCE: 2

```
Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
                20                  25                  30

Phe Ser Thr Pro Pro Lys Thr Pro Thr Pro Leu Phe His Arg Pro Leu
            35                  40                  45

Gln Ile Ser Ser Gln Ser His Lys Ser Ser Ala Ile Lys Thr Gln
        50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Pro Arg Arg Met Ile
            180                 185                 190

Gly Thr Asp Ala Phe Gln Glu Thr Pro Ile Val Glu Val Thr Arg Ser
        195                 200                 205

Ile Thr Lys His Asn Tyr Leu Val Leu Asp Val Glu Asp Ile Pro Arg
210                 215                 220

Ile Val Lys Glu Ala Phe Phe Leu Ala Asn Ser Gly Arg Pro Gly Pro
225                 230                 235                 240

Val Leu Ile Asp Leu Pro Lys Asp Ile Gln Gln Gln Leu Val Val Pro
                245                 250                 255

Asp Trp Asp Arg Pro Phe Lys Leu Gly Gly Tyr Met Ser Arg Leu Pro
            260                 265                 270

Lys Ser Lys Phe Ser Thr Asn Glu Val Gly Leu Leu Glu Gln Ile Val
        275                 280                 285

Arg Leu Met Ser Glu Ser Lys Lys Pro Val Leu Tyr Val Gly Gly Gly
290                 295                 300

Cys Leu Asn Ser Ser Glu Glu Leu Arg Arg Phe Val Glu Leu Thr Gly
305                 310                 315                 320

Ile Pro Val Ala Ser Thr Leu Met Gly Leu Gly Ser Tyr Pro Cys Asn
                325                 330                 335

Asp Glu Leu Ser Leu His Met Leu Gly Met His Gly Thr Val Tyr Ala
            340                 345                 350

Asn Tyr Ala Val Asp Lys Ala Asp Leu Leu Leu Ala Phe Gly Val Arg
        355                 360                 365
```

```
Phe Asp Asp Arg Val Thr Gly Lys Leu Glu Ala Phe Ala Ser Arg Ala
            370                 375                 380

Lys Ile Val His Ile Asp Ile Asp Ser Ala Glu Ile Gly Lys Asn Lys
385                 390                 395                 400

Gln Pro His Val Ser Ile Cys Ala Asp Val Lys Leu Ala Leu Arg Gly
                405                 410                 415

Met Asn Lys Ile Leu Glu Ser Arg Ile Gly Lys Leu Asn Leu Asp Phe
            420                 425                 430

Ser Lys Trp Arg Glu Glu Leu Gly Glu Gln Lys Lys Glu Phe Pro Leu
435                 440                 445

Ser Phe Lys Thr Phe Gly Asp Ala Ile Pro Pro Gln Tyr Ala Ile Gln
450                 455                 460

Val Leu Asp Glu Leu Thr Asn Gly Asn Ala Ile Ile Ser Thr Gly Val
465                 470                 475                 480

Gly Gln His Gln Met Trp Ala Ala Gln His Tyr Lys Tyr Arg Asn Pro
                485                 490                 495

Arg Gln Trp Leu Thr Ser Gly Gly Leu Gly Ala Met Gly Phe Gly Leu
            500                 505                 510

Pro Ala Ala Ile Gly Ala Ala Val Ala Arg Pro Asp Ala Val Val Val
            515                 520                 525

Asp Ile Asp Gly Asp Gly Ser Phe Ile Met Asn Val Gln Glu Leu Ala
530                 535                 540

Thr Ile Arg Val Glu Asn Leu Pro Val Lys Ile Met Leu Leu Asn Asn
545                 550                 555                 560

Gln His Leu Gly Met Val Val Gln Trp Glu Asp Arg Phe Tyr Lys Ala
                565                 570                 575

Asn Arg Ala His Thr Tyr Leu Gly Asn Pro Ser Lys Ser Ala Asp Ile
            580                 585                 590

Phe Pro Asp Met Leu Lys Phe Ala Glu Ala Cys Asp Ile Pro Ser Ala
            595                 600                 605

Arg Val Ser Asn Val Ala Asp Leu Arg Ala Ala Ile Gln Thr Met Leu
            610                 615                 620

Asp Thr Pro Gly Pro Tyr Leu Leu Asp Val Ile Val Pro His Gln Glu
625                 630                 635                 640

His Val Leu Pro Met Ile Pro Ser Gly Ala Gly Phe Lys Asp Thr Ile
                645                 650                 655

Thr Glu Gly Asp Gly Arg Thr Ser Tyr
            660                 665

<210> SEQ ID NO 3
<211> LENGTH: 1998
<212> TYPE: DNA
<213> ORGANISM: Beta Vulgaris
<220> FEATURE:
<221> NAME/KEY: misc_feature
<222> LOCATION: (1)..(1998)
<223> OTHER INFORMATION: 4D6834 W574
<220> FEATURE:
<221> NAME/KEY: CDS
<222> LOCATION: (1)..(1998)
<223> OTHER INFORMATION: 4D6834 W574

<400> SEQUENCE: 3 atg gcg gct acc ttc aca aac cca aca ttt tcc cct tcc tca act cca     48
Met Ala Ala Thr Phe Thr Asn Pro Thr Phe Ser Pro Ser Ser Thr Pro
1               5                   10                  15 tta acc aaa acc cta aaa tcc caa tct tcc atc tct tca acc ctc ccc    96
Leu Thr Lys Thr Leu Lys Ser Gln Ser Ser Ile Ser Ser Thr Leu Pro
```

```
                 20                  25                  30
ttt tcc acc cct ccc aaa acc cca act cca ctc ttt cac cgt ccc ctc      144
Phe Ser Thr Pro Pro Lys Thr Pro Thr Pro Leu Phe His Arg Pro Leu
            35                  40                  45 caa atc tca tcc tcc caa tcc cac aaa tca tcc gcc att aaa aca caa      192
Gln Ile Ser Ser Ser Gln Ser His Lys Ser Ser Ala Ile Lys Thr Gln
 50                  55                  60 act caa gca cct tct tct cca gct att gaa gat tca tct ttc gtt tct      240
Thr Gln Ala Pro Ser Ser Pro Ala Ile Glu Asp Ser Ser Phe Val Ser
 65                  70                  75                  80 cga ttt ggc cct gat gaa ccc aga aaa ggg tcc gat gtc ctc gtt gaa      288
Arg Phe Gly Pro Asp Glu Pro Arg Lys Gly Ser Asp Val Leu Val Glu
                 85                  90                  95 gct ctt gag cgt gaa ggt gtt acc aat gtg ttt gct tac cct ggt ggt      336
Ala Leu Glu Arg Glu Gly Val Thr Asn Val Phe Ala Tyr Pro Gly Gly
            100                 105                 110 gca tct atg gaa atc cac caa gct ctc aca cgc tct aaa acc atc cgc      384
Ala Ser Met Glu Ile His Gln Ala Leu Thr Arg Ser Lys Thr Ile Arg
        115                 120                 125 aat gtc ctc cct cgc cat gaa caa ggc ggg gtt ttc gcc gcc gag gga      432
Asn Val Leu Pro Arg His Glu Gln Gly Gly Val Phe Ala Ala Glu Gly
130                 135                 140 tat gct aga gct act gga aag gtt ggt gtc tgc att gcg act tct ggt      480
Tyr Ala Arg Ala Thr Gly Lys Val Gly Val Cys Ile Ala Thr Ser Gly
145                 150                 155                 160 cct ggt gct acc aac ctc gta tca ggt ctt gct gac gct ctc ctt gat      528
Pro Gly Ala Thr Asn Leu Val Ser Gly Leu Ala Asp Ala Leu Leu Asp
                165                 170                 175 tct gtc cct ctt gtt gcc atc act ggc caa gtt cca cgc cgt atg att      576
Ser Val Pro Leu Val Ala Ile Thr Gly Gln Val Pro Arg Arg Met Ile
            180                 185                 190 ggc act gat gct ttt cag gag act cca att gtt gag gtg aca agg tct      624
Gly Thr Asp Ala Phe Gln Glu Thr Pro Ile Val Glu Val Thr Arg Ser
        195                 200                 205 att act aag cat aat tat tta gtt ttg gat gta gag gat att cct aga      672
Ile Thr Lys His Asn Tyr Leu Val Leu Asp Val Glu Asp Ile Pro Arg
210                 215                 220 att gtt aag gaa gcc ttt ttt tta gct aat tct ggt agg cct gga cct      720
Ile Val Lys Glu Ala Phe Phe Leu Ala Asn Ser Gly Arg Pro Gly Pro
225                 230                 235                 240 gtt ttg att gat ctt cct aaa gat att cag cag caa ttg gtt gtt cct      768
Val Leu Ile Asp Leu Pro Lys Asp Ile Gln Gln Gln Leu Val Val Pro
                245                 250                 255 gat tgg gat agg cct ttt aag ttg ggt ggg tat atg tct agg ctg cca      816
Asp Trp Asp Arg Pro Phe Lys Leu Gly Gly Tyr Met Ser Arg Leu Pro
            260                 265                 270 aag tcc aag ttt tcg acg aat gag gtt gga ctt ctt gag cag att gtg      864
Lys Ser Lys Phe Ser Thr Asn Glu Val Gly Leu Leu Glu Gln Ile Val
        275                 280                 285 agg ttg atg agt gag tcg aag aag cct gtc ttg tat gtg gga ggt ggg      912
Arg Leu Met Ser Glu Ser Lys Lys Pro Val Leu Tyr Val Gly Gly Gly
290                 295                 300 tgt ttg aat tct agt gag gag ttg agg aga ttt gtt gag ttg aca ggg      960
Cys Leu Asn Ser Ser Glu Glu Leu Arg Arg Phe Val Glu Leu Thr Gly
305                 310                 315                 320 att ccg gtg gct agt act ttg atg ggg ttg ggg tct tac cct tgt aat     1008
Ile Pro Val Ala Ser Thr Leu Met Gly Leu Gly Ser Tyr Pro Cys Asn
                325                 330                 335 gat gaa ctg tct ctt cat atg ttg ggg atg cac ggg act gtt tat gcc     1056
```

```
                Asp Glu Leu Ser Leu His Met Leu Gly Met His Gly Thr Val Tyr Ala
                                340                 345                 350 aat tat gcg gtg gat aag gcg gat ttg ttg ctt gct ttc ggg gtt agg              1104
Asn Tyr Ala Val Asp Lys Ala Asp Leu Leu Leu Ala Phe Gly Val Arg
        355                 360                 365 ttt gat gat cgt gtg acc ggg aag ctc gag gcg ttt gct agc cgt gct              1152
Phe Asp Asp Arg Val Thr Gly Lys Leu Glu Ala Phe Ala Ser Arg Ala
370                 375                 380 aag att gtg cat att gat att gac tct gct gag att ggg aag aac aag              1200
Lys Ile Val His Ile Asp Ile Asp Ser Ala Glu Ile Gly Lys Asn Lys
385                 390                 395                 400 cag ccc cat gtg tcc att tgt gct gat gtt aaa ttg gca ttg cgg ggt              1248
Gln Pro His Val Ser Ile Cys Ala Asp Val Lys Leu Ala Leu Arg Gly
                405                 410                 415 atg aat aag att ctg gag tct aga ata ggg aag ctg aat ttg gat ttc              1296
Met Asn Lys Ile Leu Glu Ser Arg Ile Gly Lys Leu Asn Leu Asp Phe
            420                 425                 430 tcc aag tgg aga gaa gaa tta ggt gag cag aag aag gaa ttc cca ctg              1344
Ser Lys Trp Arg Glu Glu Leu Gly Glu Gln Lys Lys Glu Phe Pro Leu
        435                 440                 445 agt ttt aag aca ttt ggg gat gca att cct cca caa tat gcc att cag              1392
Ser Phe Lys Thr Phe Gly Asp Ala Ile Pro Pro Gln Tyr Ala Ile Gln
450                 455                 460 gtg ctt gat gag ttg acc aat ggt aat gct att ata agt act ggt gtt              1440
Val Leu Asp Glu Leu Thr Asn Gly Asn Ala Ile Ile Ser Thr Gly Val
465                 470                 475                 480 ggg cag cac caa atg tgg gct gcg cag cat tac aag tac aga aac cct              1488
Gly Gln His Gln Met Trp Ala Ala Gln His Tyr Lys Tyr Arg Asn Pro
                485                 490                 495 cgc caa tgg ctg acc tct ggt ggg ttg ggg gct atg ggg ttt ggg cta              1536
Arg Gln Trp Leu Thr Ser Gly Gly Leu Gly Ala Met Gly Phe Gly Leu
            500                 505                 510 cca gcc gcc att gga gct gca gtt gct cga cca gat gca gtg gtt gtc              1584
Pro Ala Ala Ile Gly Ala Ala Val Ala Arg Pro Asp Ala Val Val Val
        515                 520                 525 gat att gat ggg gat ggc agt ttt att atg aat gtt caa gag ttg gct              1632
Asp Ile Asp Gly Asp Gly Ser Phe Ile Met Asn Val Gln Glu Leu Ala
530                 535                 540 aca att agg gtg gaa aat ctc cca gtt aag ata atg ctg cta aac aat              1680
Thr Ile Arg Val Glu Asn Leu Pro Val Lys Ile Met Leu Leu Asn Asn
545                 550                 555                 560 caa cat tta ggt atg gtt gtc caa ttg gaa gat agg ttc tat aaa gct              1728
Gln His Leu Gly Met Val Val Gln Leu Glu Asp Arg Phe Tyr Lys Ala
                565                 570                 575 aac cgg gca cat aca tac ctt gga aac cct tcc aaa tct gct gat atc              1776
Asn Arg Ala His Thr Tyr Leu Gly Asn Pro Ser Lys Ser Ala Asp Ile
            580                 585                 590 ttc cct gat atg ctc aaa ttc gct gag gca tgt gat att cct tct gcc              1824
Phe Pro Asp Met Leu Lys Phe Ala Glu Ala Cys Asp Ile Pro Ser Ala
        595                 600                 605 cgt gtt agc aac gtg gct gat ttg agg gcc gcc att caa aca atg ttg              1872
Arg Val Ser Asn Val Ala Asp Leu Arg Ala Ala Ile Gln Thr Met Leu
610                 615                 620 gat act cca ggg ccg tac ctg ctc gat gtg att gta ccg cat caa gag              1920
Asp Thr Pro Gly Pro Tyr Leu Leu Asp Val Ile Val Pro His Gln Glu
625                 630                 635                 640 cat gtg ttg cct atg att cca agt ggt gcc ggt ttc aag gat acc att              1968
His Val Leu Pro Met Ile Pro Ser Gly Ala Gly Phe Lys Asp Thr Ile
                645                 650                 655
```

```
aca gag ggt gat gga aga acc tct tat tga                                    1998
Thr Glu Gly Asp Gly Arg Thr Ser Tyr
        660                 665

<210> SEQ ID NO 4
<211> LENGTH: 665
<212> TYPE: PRT
<213> ORGANISM: Beta Vulgaris

<400> SEQUENCE: 4

Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
    130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Pro Arg Arg Met Ile
            180                 185                 190

Gly Thr Asp Ala Phe Gln Glu Thr Pro Ile Val Glu Val Thr Arg Ser
        195                 200                 205

Ile Thr Lys His Asn Tyr Leu Val Leu Asp Val Glu Asp Ile Pro Arg
    210                 215                 220

Ile Val Lys Glu Ala Phe Phe Leu Ala Asn Ser Gly Arg Pro Gly Pro
225                 230                 235                 240

Val Leu Ile Asp Leu Pro Lys Asp Ile Gln Gln Gln Leu Val Val Pro
                245                 250                 255

Asp Trp Asp Arg Pro Phe Lys Leu Gly Gly Tyr Met Ser Arg Leu Pro
            260                 265                 270

Lys Ser Lys Phe Ser Thr Asn Glu Val Gly Leu Leu Glu Gln Ile Val
        275                 280                 285

Arg Leu Met Ser Glu Ser Lys Lys Pro Val Leu Tyr Val Gly Gly Gly
    290                 295                 300

Cys Leu Asn Ser Ser Glu Glu Leu Arg Arg Phe Val Glu Leu Thr Gly
305                 310                 315                 320

Ile Pro Val Ala Ser Thr Leu Met Gly Leu Gly Ser Tyr Pro Cys Asn
                325                 330                 335

Asp Glu Leu Ser Leu His Met Leu Gly Met His Gly Thr Val Tyr Ala
            340                 345                 350

Asn Tyr Ala Val Asp Lys Ala Asp Leu Leu Leu Ala Phe Gly Val Arg
```

| | | | | | | | | | | | |
|---|---|---|---|---|---|---|---|---|---|---|---|
| | | 355 | | | 360 | | | 365 | | | |
| Phe | Asp | Asp | Arg | Val | Thr | Gly | Lys | Leu | Glu | Ala | Phe | Ala | Ser | Arg | Ala |
| 370 | | | | | 375 | | | | | 380 | |

Phe Asp Asp Arg Val Thr Gly Lys Leu Glu Ala Phe Ala Ser Arg Ala
   370                 375                 380

Lys Ile Val His Ile Asp Ile Asp Ser Ala Glu Ile Gly Lys Asn Lys
385                 390                 395                 400

Gln Pro His Val Ser Ile Cys Ala Asp Val Lys Leu Ala Leu Arg Gly
            405                 410                 415

Met Asn Lys Ile Leu Glu Ser Arg Ile Gly Lys Leu Asn Leu Asp Phe
        420                 425                 430

Ser Lys Trp Arg Glu Glu Leu Gly Glu Gln Lys Lys Glu Phe Pro Leu
    435                 440                 445

Ser Phe Lys Thr Phe Gly Asp Ala Ile Pro Pro Gln Tyr Ala Ile Gln
450                 455                 460

Val Leu Asp Glu Leu Thr Asn Gly Asn Ala Ile Ile Ser Thr Gly Val
465                 470                 475                 480

Gly Gln His Gln Met Trp Ala Ala Gln His Tyr Lys Tyr Arg Asn Pro
                485                 490                 495

Arg Gln Trp Leu Thr Ser Gly Gly Leu Gly Ala Met Gly Phe Gly Leu
            500                 505                 510

Pro Ala Ala Ile Gly Ala Ala Val Ala Arg Pro Asp Ala Val Val Val
        515                 520                 525

Asp Ile Asp Gly Asp Gly Ser Phe Ile Met Asn Val Gln Glu Leu Ala
    530                 535                 540

Thr Ile Arg Val Glu Asn Leu Pro Val Lys Ile Met Leu Leu Asn Asn
545                 550                 555                 560

Gln His Leu Gly Met Val Val Gln Leu Glu Asp Arg Phe Tyr Lys Ala
                565                 570                 575

Asn Arg Ala His Thr Tyr Leu Gly Asn Pro Ser Lys Ser Ala Asp Ile
            580                 585                 590

Phe Pro Asp Met Leu Lys Phe Ala Glu Ala Cys Asp Ile Pro Ser Ala
        595                 600                 605

Arg Val Ser Asn Val Ala Asp Leu Arg Ala Ala Ile Gln Thr Met Leu
    610                 615                 620

Asp Thr Pro Gly Pro Tyr Leu Leu Asp Val Ile Val Pro His Gln Glu
625                 630                 635                 640

His Val Leu Pro Met Ile Pro Ser Gly Ala Gly Phe Lys Asp Thr Ile
                645                 650                 655

Thr Glu Gly Asp Gly Arg Thr Ser Tyr
            660                 665

<210> SEQ ID NO 5
<211> LENGTH: 1998
<212> TYPE: DNA
<213> ORGANISM: Beta Vulgaris
<220> FEATURE:
<221> NAME/KEY: misc_feature
<222> LOCATION: (1)..(1998)
<223> OTHER INFORMATION: Pro Mutant
<220> FEATURE:
<221> NAME/KEY: CDS
<222> LOCATION: (1)..(1998)

<400> SEQUENCE: 5 atg gcg gct acc ttc aca aac cca aca ttt tcc cct tcc tca act cca      48
Met Ala Ala Thr Phe Thr Asn Pro Thr Phe Ser Pro Ser Ser Thr Pro
1               5                   10                  15 tta acc aaa acc cta aaa tcc caa tct tcc atc tct tca acc ctc ccc      96

```
Leu Thr Lys Thr Leu Lys Ser Gln Ser Ser Ile Ser Ser Thr Leu Pro
            20                  25                  30 ttt tcc acc cct ccc aaa acc cca act cca ctc ttt cac cgt ccc ctc      144
Phe Ser Thr Pro Pro Lys Thr Pro Thr Pro Leu Phe His Arg Pro Leu
            35                  40                  45 caa atc tca tcc tcc caa tcc cac aaa tca tcc gcc att aaa aca caa      192
Gln Ile Ser Ser Ser Gln Ser His Lys Ser Ser Ala Ile Lys Thr Gln
        50                  55                  60 act caa gca cct tct tct cca gct att gaa gat tca tct ttc gtt tct      240
Thr Gln Ala Pro Ser Ser Pro Ala Ile Glu Asp Ser Ser Phe Val Ser
65                  70                  75                  80 cga ttt ggc cct gat gaa ccc aga aaa ggg tcc gat gtc ctc gtt gaa      288
Arg Phe Gly Pro Asp Glu Pro Arg Lys Gly Ser Asp Val Leu Val Glu
                85                  90                  95 gct ctt gag cgt gaa ggt gtt acc aat gtg ttt gct tac cct ggt ggt      336
Ala Leu Glu Arg Glu Gly Val Thr Asn Val Phe Ala Tyr Pro Gly Gly
            100                 105                 110 gca tct atg gaa atc cac caa gct ctc aca cgc tct aaa acc atc cgc      384
Ala Ser Met Glu Ile His Gln Ala Leu Thr Arg Ser Lys Thr Ile Arg
        115                 120                 125 aat gtc ctc cct cgc cat gaa caa ggc ggg gtt ttc gcc gcc gag gga      432
Asn Val Leu Pro Arg His Glu Gln Gly Gly Val Phe Ala Ala Glu Gly
    130                 135                 140 tat gct aga gct act gga aag gtt ggt gtc tgc att gcg act tct ggt      480
Tyr Ala Arg Ala Thr Gly Lys Val Gly Val Cys Ile Ala Thr Ser Gly
145                 150                 155                 160 cct ggt gct acc aac ctc gta tca ggt ctt gct gac gct ctc ctt gat      528
Pro Gly Ala Thr Asn Leu Val Ser Gly Leu Ala Asp Ala Leu Leu Asp
                165                 170                 175 tct gtc cct ctt gtt gcc atc act ggc caa gtt tca cgc cgt atg att      576
Ser Val Pro Leu Val Ala Ile Thr Gly Gln Val Ser Arg Arg Met Ile
            180                 185                 190 ggc act gat gct ttt cag gag act cca att gtt gag gtg aca agg tct      624
Gly Thr Asp Ala Phe Gln Glu Thr Pro Ile Val Glu Val Thr Arg Ser
        195                 200                 205 att act aag cat aat tat tta gtt ttg gat gta gag gat att cct aga      672
Ile Thr Lys His Asn Tyr Leu Val Leu Asp Val Glu Asp Ile Pro Arg
    210                 215                 220 att gtt aag gaa gcc ttt ttt tta gct aat tct ggt agg cct gga cct      720
Ile Val Lys Glu Ala Phe Phe Leu Ala Asn Ser Gly Arg Pro Gly Pro
225                 230                 235                 240 gtt ttg att gat ctt cct aaa gat att cag cag caa ttg gtt gtt cct      768
Val Leu Ile Asp Leu Pro Lys Asp Ile Gln Gln Gln Leu Val Val Pro
                245                 250                 255 gat tgg gat agg cct ttt aag ttg ggt ggg tat atg tct agg ctg cca      816
Asp Trp Asp Arg Pro Phe Lys Leu Gly Gly Tyr Met Ser Arg Leu Pro
            260                 265                 270 aag tcc aag ttt tcg acg aat gag gtt gga ctt ctt gag cag att gtg      864
Lys Ser Lys Phe Ser Thr Asn Glu Val Gly Leu Leu Glu Gln Ile Val
        275                 280                 285 agg ttg atg agt gag tcg aag aag cct gtc ttg tat gtg gga ggt ggg      912
Arg Leu Met Ser Glu Ser Lys Lys Pro Val Leu Tyr Val Gly Gly Gly
    290                 295                 300 tgt ttg aat tct agt gag gag ttg agg aga ttt gtt gag ttg aca ggg      960
Cys Leu Asn Ser Ser Glu Glu Leu Arg Arg Phe Val Glu Leu Thr Gly
305                 310                 315                 320 att ccg gtg gct agt act ttg atg ggg ttg ggg tct tac cct tgt aat     1008
Ile Pro Val Ala Ser Thr Leu Met Gly Leu Gly Ser Tyr Pro Cys Asn
                325                 330                 335
```

```
gat gaa ctg tct ctt cat atg ttg ggg atg cac ggg act gtt tat gcc   1056
Asp Glu Leu Ser Leu His Met Leu Gly Met His Gly Thr Val Tyr Ala
            340                 345                 350 aat tat gcg gtg gat aag gcg gat ttg ttg ctt gct ttc ggg gtt agg   1104
Asn Tyr Ala Val Asp Lys Ala Asp Leu Leu Leu Ala Phe Gly Val Arg
        355                 360                 365 ttt gat gat cgt gtg acc ggg aag ctc gag gcg ttt gct agc cgt gct   1152
Phe Asp Asp Arg Val Thr Gly Lys Leu Glu Ala Phe Ala Ser Arg Ala
    370                 375                 380 aag att gtg cat att gat att gac tct gct gag att ggg aag aac aag   1200
Lys Ile Val His Ile Asp Ile Asp Ser Ala Glu Ile Gly Lys Asn Lys
385                 390                 395                 400 cag ccc cat gtg tcc att tgt gct gat gtt aaa ttg gca ttg cgg ggt   1248
Gln Pro His Val Ser Ile Cys Ala Asp Val Lys Leu Ala Leu Arg Gly
            405                 410                 415 atg aat aag att ctg gag tct aga ata ggg aag ctg aat ttg gat ttc   1296
Met Asn Lys Ile Leu Glu Ser Arg Ile Gly Lys Leu Asn Leu Asp Phe
        420                 425                 430 tcc aag tgg aga gaa gaa tta ggt gag cag aag aag gaa ttc cca ctg   1344
Ser Lys Trp Arg Glu Glu Leu Gly Glu Gln Lys Lys Glu Phe Pro Leu
    435                 440                 445 agt ttt aag aca ttt ggg gat gca att cct cca caa tat gcc att cag   1392
Ser Phe Lys Thr Phe Gly Asp Ala Ile Pro Pro Gln Tyr Ala Ile Gln
450                 455                 460 gtg ctt gat gag ttg acc aat ggt aat gct att ata agt act ggt gtt   1440
Val Leu Asp Glu Leu Thr Asn Gly Asn Ala Ile Ile Ser Thr Gly Val
465                 470                 475                 480 ggg cag cac caa atg tgg gct gcg cag cat tac aag tac aga aac cct   1488
Gly Gln His Gln Met Trp Ala Ala Gln His Tyr Lys Tyr Arg Asn Pro
            485                 490                 495 cgc caa tgg ctg acc tct ggt ggg ttg ggg gct atg ggg ttt ggg cta   1536
Arg Gln Trp Leu Thr Ser Gly Gly Leu Gly Ala Met Gly Phe Gly Leu
        500                 505                 510 cca gcc gcc att gga gct gca gtt gct cga cca gat gca gtg gtt gtc   1584
Pro Ala Ala Ile Gly Ala Ala Val Ala Arg Pro Asp Ala Val Val Val
    515                 520                 525 gat att gat ggg gat ggc agt ttt att atg aat gtt caa gag ttg gct   1632
Asp Ile Asp Gly Asp Gly Ser Phe Ile Met Asn Val Gln Glu Leu Ala
530                 535                 540 aca att agg gtg gaa aat ctc cca gtt aag ata atg ctg cta aac aat   1680
Thr Ile Arg Val Glu Asn Leu Pro Val Lys Ile Met Leu Leu Asn Asn
545                 550                 555                 560 caa cat tta ggt atg gtt gtc caa tgg gaa gat agg ttc tat aaa gct   1728
Gln His Leu Gly Met Val Val Gln Trp Glu Asp Arg Phe Tyr Lys Ala
            565                 570                 575 aac cgg gca cat aca tac ctt gga aac cct tcc aaa tct gct gat atc   1776
Asn Arg Ala His Thr Tyr Leu Gly Asn Pro Ser Lys Ser Ala Asp Ile
        580                 585                 590 ttc cct gat atg ctc aaa ttc gct gag gca tgt gat att cct tct gcc   1824
Phe Pro Asp Met Leu Lys Phe Ala Glu Ala Cys Asp Ile Pro Ser Ala
    595                 600                 605 cgt gtt agc aac gtg gct gat ttg agg gcc gcc att caa aca atg ttg   1872
Arg Val Ser Asn Val Ala Asp Leu Arg Ala Ala Ile Gln Thr Met Leu
610                 615                 620 gat act cca ggg ccg tac ctg ctc gat gtg att gta ccg cat caa gag   1920
Asp Thr Pro Gly Pro Tyr Leu Leu Asp Val Ile Val Pro His Gln Glu
625                 630                 635                 640 cat gtg ttg cct atg att cca agt ggt gcc ggt ttc aag gat acc att   1968
His Val Leu Pro Met Ile Pro Ser Gly Ala Gly Phe Lys Asp Thr Ile
            645                 650                 655
```

```
aca gag ggt gat gga aga acc tct tat tga                                    1998
Thr Glu Gly Asp Gly Arg Thr Ser Tyr
            660                 665

<210> SEQ ID NO 6
<211> LENGTH: 665
<212> TYPE: PRT
<213> ORGANISM: Beta Vulgaris

<400> SEQUENCE: 6

Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
    130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Ser Arg Arg Met Ile
            180                 185                 190

Gly Thr Asp Ala Phe Gln Glu Thr Pro Ile Val Glu Val Thr Arg Ser
        195                 200                 205

Ile Thr Lys His Asn Tyr Leu Val Leu Asp Val Glu Asp Ile Pro Arg
    210                 215                 220

Ile Val Lys Glu Ala Phe Phe Leu Ala Asn Ser Gly Arg Pro Gly Pro
225                 230                 235                 240

Val Leu Ile Asp Leu Pro Lys Asp Ile Gln Gln Leu Val Val Pro
                245                 250                 255

Asp Trp Asp Arg Pro Phe Lys Leu Gly Gly Tyr Met Ser Arg Leu Pro
                260                 265                 270

Lys Ser Lys Phe Ser Thr Asn Glu Val Gly Leu Leu Glu Gln Ile Val
            275                 280                 285

Arg Leu Met Ser Glu Ser Lys Lys Pro Val Leu Tyr Val Gly Gly Gly
        290                 295                 300

Cys Leu Asn Ser Ser Glu Glu Leu Arg Arg Phe Val Glu Leu Thr Gly
305                 310                 315                 320

Ile Pro Val Ala Ser Thr Leu Met Gly Leu Gly Ser Tyr Pro Cys Asn
                325                 330                 335

Asp Glu Leu Ser Leu His Met Leu Gly Met His Gly Thr Val Tyr Ala
            340                 345                 350
```

```
Asn Tyr Ala Val Asp Lys Ala Asp Leu Leu Ala Phe Gly Val Arg
            355                 360                 365

Phe Asp Asp Arg Val Thr Gly Lys Leu Glu Ala Phe Ala Ser Arg Ala
    370                 375                 380

Lys Ile Val His Ile Asp Ile Asp Ser Ala Glu Ile Gly Lys Asn Lys
385                 390                 395                 400

Gln Pro His Val Ser Ile Cys Ala Asp Val Lys Leu Ala Leu Arg Gly
                405                 410                 415

Met Asn Lys Ile Leu Glu Ser Arg Ile Gly Lys Leu Asn Leu Asp Phe
            420                 425                 430

Ser Lys Trp Arg Glu Glu Leu Gly Glu Gln Lys Lys Glu Phe Pro Leu
            435                 440                 445

Ser Phe Lys Thr Phe Gly Asp Ala Ile Pro Pro Gln Tyr Ala Ile Gln
    450                 455                 460

Val Leu Asp Glu Leu Thr Asn Gly Asn Ala Ile Ile Ser Thr Gly Val
465                 470                 475                 480

Gly Gln His Gln Met Trp Ala Ala Gln His Tyr Lys Tyr Arg Asn Pro
                485                 490                 495

Arg Gln Trp Leu Thr Ser Gly Gly Leu Gly Ala Met Gly Phe Gly Leu
            500                 505                 510

Pro Ala Ala Ile Gly Ala Ala Val Ala Arg Pro Asp Ala Val Val Val
            515                 520                 525

Asp Ile Asp Gly Asp Gly Ser Phe Ile Met Asn Val Gln Glu Leu Ala
    530                 535                 540

Thr Ile Arg Val Glu Asn Leu Pro Val Lys Ile Met Leu Leu Asn Asn
545                 550                 555                 560

Gln His Leu Gly Met Val Val Gln Trp Glu Asp Arg Phe Tyr Lys Ala
                565                 570                 575

Asn Arg Ala His Thr Tyr Leu Gly Asn Pro Ser Lys Ser Ala Asp Ile
            580                 585                 590

Phe Pro Asp Met Leu Lys Phe Ala Glu Ala Cys Asp Ile Pro Ser Ala
            595                 600                 605

Arg Val Ser Asn Val Ala Asp Leu Arg Ala Ala Ile Gln Thr Met Leu
    610                 615                 620

Asp Thr Pro Gly Pro Tyr Leu Leu Asp Val Ile Val Pro His Gln Glu
625                 630                 635                 640

His Val Leu Pro Met Ile Pro Ser Gly Ala Gly Phe Lys Asp Thr Ile
                645                 650                 655

Thr Glu Gly Asp Gly Arg Thr Ser Tyr
            660                 665

<210> SEQ ID NO 7
<211> LENGTH: 1998
<212> TYPE: DNA
<213> ORGANISM: Beta Vulgaris
<220> FEATURE:
<221> NAME/KEY: misc_feature
<222> LOCATION: (1)..(1998)
<223> OTHER INFORMATION: 4D6834 a12 WT
<220> FEATURE:
<221> NAME/KEY: CDS
<222> LOCATION: (1)..(1998)

<400> SEQUENCE: 7 atg gcg gct acc ttc aca aac cca aca ttt tcc cct tcc tca act caa     48
Met Ala Ala Thr Phe Thr Asn Pro Thr Phe Ser Pro Ser Ser Thr Gln
1               5                   10                  15
```

```
                                                                         -continued tta acc aaa acc cta aaa tcc caa tct tcc att tct tca acc ctc ccc           96
Leu Thr Lys Thr Leu Lys Ser Gln Ser Ser Ile Ser Ser Thr Leu Pro
         20                  25                  30 ttt tcc acc cct ccc aaa acc cca act cca ctc ttt cac cgt ccc ctc          144
Phe Ser Thr Pro Pro Lys Thr Pro Thr Pro Leu Phe His Arg Pro Leu
         35                  40                  45 caa atc tca tcc tcc caa tcc cac aaa tca tcc gcc att aaa aca caa          192
Gln Ile Ser Ser Ser Gln Ser His Lys Ser Ser Ala Ile Lys Thr Gln
         50                  55                  60 act caa gca cct tct tct cca gct att gaa gat tca tct ttc gtt tct          240
Thr Gln Ala Pro Ser Ser Pro Ala Ile Glu Asp Ser Ser Phe Val Ser
 65                  70                  75                  80 cga ttt ggc cct gat gaa ccc aga aaa ggg tcc gat gtc ctc gtt gaa          288
Arg Phe Gly Pro Asp Glu Pro Arg Lys Gly Ser Asp Val Leu Val Glu
                 85                  90                  95 gct ctt gag cgt gaa ggt gtt acc aat gtg ttt gct tac cct ggt ggt          336
Ala Leu Glu Arg Glu Gly Val Thr Asn Val Phe Ala Tyr Pro Gly Gly
                100                 105                 110 gca tct atg gaa atc cac caa gct ctg acg cgc tct aaa acc atc cgc          384
Ala Ser Met Glu Ile His Gln Ala Leu Thr Arg Ser Lys Thr Ile Arg
            115                 120                 125 aat gtc ctc ccc cgc cat gaa caa ggc ggg gtt ttc gcc gcc gag gga          432
Asn Val Leu Pro Arg His Glu Gln Gly Gly Val Phe Ala Ala Glu Gly
        130                 135                 140 tat gct aga gct act gga aag gtt ggt gtc tgc att gcg act tct ggt          480
Tyr Ala Arg Ala Thr Gly Lys Val Gly Val Cys Ile Ala Thr Ser Gly
145                 150                 155                 160 cct ggt gct acc aac ctc gta tca ggt ctt gct gac gct ctc ctt gat          528
Pro Gly Ala Thr Asn Leu Val Ser Gly Leu Ala Asp Ala Leu Leu Asp
                165                 170                 175 tct gtc cct ctt gtt gcc atc act ggc caa gtt cca cgc cgt atg att          576
Ser Val Pro Leu Val Ala Ile Thr Gly Gln Val Pro Arg Arg Met Ile
            180                 185                 190 ggc act gat gct ttt cag gag act cca att gtt gag gta aca agg tct          624
Gly Thr Asp Ala Phe Gln Glu Thr Pro Ile Val Glu Val Thr Arg Ser
        195                 200                 205 att act aag cat aat tat ttg gtt ttg gat gta gaa gat att cct aga          672
Ile Thr Lys His Asn Tyr Leu Val Leu Asp Val Glu Asp Ile Pro Arg
210                 215                 220 att gtt aag gaa gcc ttt ttt tta gct aat tct ggc agg cct gga cct          720
Ile Val Lys Glu Ala Phe Phe Leu Ala Asn Ser Gly Arg Pro Gly Pro
225                 230                 235                 240 gtt ttg att gat ctt cct aaa gat att cag cag caa ctg gtt gtt cct          768
Val Leu Ile Asp Leu Pro Lys Asp Ile Gln Gln Gln Leu Val Val Pro
                245                 250                 255 gat tgg gat agg cct ttt aag ttg ggt ggg tat atg tct agg ctg cca          816
Asp Trp Asp Arg Pro Phe Lys Leu Gly Gly Tyr Met Ser Arg Leu Pro
            260                 265                 270 aag tcc aag ttt tcg acg aat gag gtt gga ctt ctt gag cag att gtg          864
Lys Ser Lys Phe Ser Thr Asn Glu Val Gly Leu Leu Glu Gln Ile Val
        275                 280                 285 agg ttg atg agt gag tcg aag aag cct gtc ttg tat gtg gga ggt ggg          912
Arg Leu Met Ser Glu Ser Lys Lys Pro Val Leu Tyr Val Gly Gly Gly
290                 295                 300 tgt ttg aat tct agt gag gag ttg agg aga ttt gtt gag ttg aca ggg          960
Cys Leu Asn Ser Ser Glu Glu Leu Arg Arg Phe Val Glu Leu Thr Gly
305                 310                 315                 320 att ccg gtg gct agt act ttg atg ggg ttg ggg tct tac cct tgt aat         1008
Ile Pro Val Ala Ser Thr Leu Met Gly Leu Gly Ser Tyr Pro Cys Asn
                325                 330                 335
```

```
                                                          -continued gat gaa ctg tct ctt cat atg ttg ggg atg cac ggg act gtt tat gcc    1056
Asp Glu Leu Ser Leu His Met Leu Gly Met His Gly Thr Val Tyr Ala
            340                 345                 350 aat tat gcg gtg gat aag gcg gat ttg ttg ctt gct ttc ggg gtt agg    1104
Asn Tyr Ala Val Asp Lys Ala Asp Leu Leu Leu Ala Phe Gly Val Arg
    355                 360                 365 ttt gat gat cgt gtg act ggg aag ctc gag gcg ttt gct agc cgt gct    1152
Phe Asp Asp Arg Val Thr Gly Lys Leu Glu Ala Phe Ala Ser Arg Ala
370                 375                 380 aag att gtg cat att gat att gac tct gct gag att ggg aag aac aag    1200
Lys Ile Val His Ile Asp Ile Asp Ser Ala Glu Ile Gly Lys Asn Lys
385                 390                 395                 400 cag ccc cat gtg tcc att tgt gct gat gtt aaa ttg gca ttg cgg ggt    1248
Gln Pro His Val Ser Ile Cys Ala Asp Val Lys Leu Ala Leu Arg Gly
            405                 410                 415 atg aat aag att ctg gag tct aga ata ggg aag ctg aat ttg gat ttc    1296
Met Asn Lys Ile Leu Glu Ser Arg Ile Gly Lys Leu Asn Leu Asp Phe
    420                 425                 430 tcc agg tgg aga gaa gaa tta ggt gag cag aag aag gaa ttc cca ctg    1344
Ser Arg Trp Arg Glu Glu Leu Gly Glu Gln Lys Lys Glu Phe Pro Leu
435                 440                 445 agt ttt aag aca ttt ggg gat gca atc cct cca caa tat gcc att cag    1392
Ser Phe Lys Thr Phe Gly Asp Ala Ile Pro Pro Gln Tyr Ala Ile Gln
450                 455                 460 gtg ctt gat gag ttg acc aat ggt aat gct att ata agt act ggt gtt    1440
Val Leu Asp Glu Leu Thr Asn Gly Asn Ala Ile Ile Ser Thr Gly Val
465                 470                 475                 480 ggg cag cac caa atg tgg gct gcg cag cat tac aag tac aga aac cct    1488
Gly Gln His Gln Met Trp Ala Ala Gln His Tyr Lys Tyr Arg Asn Pro
            485                 490                 495 cgc caa tgg ctg acc tct ggt ggg ttg ggg gct atg ggg ttt ggg cta    1536
Arg Gln Trp Leu Thr Ser Gly Gly Leu Gly Ala Met Gly Phe Gly Leu
    500                 505                 510 cca gcc gcc att gga gct gca gtt gct cga cca gat gca gtg gtt gtc    1584
Pro Ala Ala Ile Gly Ala Ala Val Ala Arg Pro Asp Ala Val Val Val
515                 520                 525 gat att gat ggg gat ggc agt ttt att atg aat gtt caa gag ttg gct    1632
Asp Ile Asp Gly Asp Gly Ser Phe Ile Met Asn Val Gln Glu Leu Ala
530                 535                 540 aca att agg gtg gaa aat ctc cca gtt aag ata atg ctg cta aac aat    1680
Thr Ile Arg Val Glu Asn Leu Pro Val Lys Ile Met Leu Leu Asn Asn
545                 550                 555                 560 caa cat tta ggt atg gtt gtc caa tgg gaa gat agg ttc tat aaa gct    1728
Gln His Leu Gly Met Val Val Gln Trp Glu Asp Arg Phe Tyr Lys Ala
            565                 570                 575 aat cgg gca cat aca tac ctt gga aac cct tcc aaa tct gct gat atc    1776
Asn Arg Ala His Thr Tyr Leu Gly Asn Pro Ser Lys Ser Ala Asp Ile
    580                 585                 590 ttc cct gat atg ctc aaa ttc gct gag gca tgt gat att cct tct gcc    1824
Phe Pro Asp Met Leu Lys Phe Ala Glu Ala Cys Asp Ile Pro Ser Ala
595                 600                 605 cgt gtt agc aac gtg gct gat ttg agg gcc gcc att caa aca atg ttg    1872
Arg Val Ser Asn Val Ala Asp Leu Arg Ala Ala Ile Gln Thr Met Leu
610                 615                 620 gat act cca ggg ccg tac ctg ctc gat gtg att gta ccg cat caa gag    1920
Asp Thr Pro Gly Pro Tyr Leu Leu Asp Val Ile Val Pro His Gln Glu
625                 630                 635                 640 cat gtg ttg cct atg att cca agt ggt gcc ggt ttc aag gat acc att    1968
His Val Leu Pro Met Ile Pro Ser Gly Ala Gly Phe Lys Asp Thr Ile
```

```
                        645                 650                 655
aca gag ggt gat gga aga acc tct tat tga                               1998
Thr Glu Gly Asp Gly Arg Thr Ser Tyr
                        660                 665

<210> SEQ ID NO 8
<211> LENGTH: 665
<212> TYPE: PRT
<213> ORGANISM: Beta Vulgaris

<400> SEQUENCE: 8

Met Ala Ala Thr Phe Thr Asn Pro Thr Phe Ser Pro Ser Ser Thr Gln
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
    130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Pro Arg Arg Met Ile
            180                 185                 190

Gly Thr Asp Ala Phe Gln Glu Thr Pro Ile Val Glu Val Thr Arg Ser
        195                 200                 205

Ile Thr Lys His Asn Tyr Leu Val Leu Asp Val Glu Asp Ile Pro Arg
    210                 215                 220

Ile Val Lys Glu Ala Phe Phe Leu Ala Asn Ser Gly Arg Pro Gly Pro
225                 230                 235                 240

Val Leu Ile Asp Leu Pro Lys Asp Ile Gln Gln Gln Leu Val Val Pro
                245                 250                 255

Asp Trp Asp Arg Pro Phe Lys Leu Gly Gly Tyr Met Ser Arg Leu Pro
            260                 265                 270

Lys Ser Lys Phe Ser Thr Asn Glu Val Gly Leu Leu Glu Gln Ile Val
        275                 280                 285

Arg Leu Met Ser Glu Ser Lys Lys Pro Val Leu Tyr Val Gly Gly Gly
    290                 295                 300

Cys Leu Asn Ser Ser Glu Glu Leu Arg Arg Phe Val Glu Leu Thr Gly
305                 310                 315                 320

Ile Pro Val Ala Ser Thr Leu Met Gly Leu Gly Ser Tyr Pro Cys Asn
                325                 330                 335

Asp Glu Leu Ser Leu His Met Leu Gly Met His Gly Thr Val Tyr Ala
            340                 345                 350
```

```
Asn Tyr Ala Val Asp Lys Ala Asp Leu Leu Ala Phe Gly Val Arg
        355                 360                 365
Phe Asp Asp Arg Val Thr Gly Lys Leu Glu Ala Phe Ala Ser Arg Ala
        370                 375                 380
Lys Ile Val His Ile Asp Ile Asp Ser Ala Glu Ile Gly Lys Asn Lys
385                 390                 395                 400
Gln Pro His Val Ser Ile Cys Ala Asp Val Lys Leu Ala Leu Arg Gly
                405                 410                 415
Met Asn Lys Ile Leu Glu Ser Arg Ile Gly Lys Leu Asn Leu Asp Phe
                420                 425                 430
Ser Arg Trp Arg Glu Glu Leu Gly Glu Gln Lys Lys Glu Phe Pro Leu
                435                 440                 445
Ser Phe Lys Thr Phe Gly Asp Ala Ile Pro Pro Gln Tyr Ala Ile Gln
        450                 455                 460
Val Leu Asp Glu Leu Thr Asn Gly Asn Ala Ile Ile Ser Thr Gly Val
465                 470                 475                 480
Gly Gln His Gln Met Trp Ala Ala Gln His Tyr Lys Tyr Arg Asn Pro
                485                 490                 495
Arg Gln Trp Leu Thr Ser Gly Gly Leu Gly Ala Met Gly Phe Gly Leu
                500                 505                 510
Pro Ala Ala Ile Gly Ala Ala Val Ala Arg Pro Asp Ala Val Val Val
        515                 520                 525
Asp Ile Asp Gly Asp Gly Ser Phe Ile Met Asn Val Gln Glu Leu Ala
        530                 535                 540
Thr Ile Arg Val Glu Asn Leu Pro Val Lys Ile Met Leu Leu Asn Asn
545                 550                 555                 560
Gln His Leu Gly Met Val Val Gln Trp Glu Asp Arg Phe Tyr Lys Ala
                565                 570                 575
Asn Arg Ala His Thr Tyr Leu Gly Asn Pro Ser Lys Ser Ala Asp Ile
                580                 585                 590
Phe Pro Asp Met Leu Lys Phe Ala Glu Ala Cys Asp Ile Pro Ser Ala
        595                 600                 605
Arg Val Ser Asn Val Ala Asp Leu Arg Ala Ala Ile Gln Thr Met Leu
        610                 615                 620
Asp Thr Pro Gly Pro Tyr Leu Leu Asp Val Ile Val Pro His Gln Glu
625                 630                 635                 640
His Val Leu Pro Met Ile Pro Ser Gly Ala Gly Phe Lys Asp Thr Ile
                645                 650                 655
Thr Glu Gly Asp Gly Arg Thr Ser Tyr
                660                 665
```